(12) United States Patent
Chung et al.

(10) Patent No.: US 11,357,783 B2
(45) Date of Patent: Jun. 14, 2022

(54) CONJUGATE OF FINASTERIDE WITH PEPTIDE

(71) Applicant: CAREGEN CO., LTD., Gyeonggi-do (KR)

(72) Inventors: Yong Ji Chung, Seoul (KR); Eun Mi Kim, Yongin-si (KR)

(73) Assignee: Caregen Co., Ltd., Gyeonggi-Do (KR)

( * ) Notice: Subject to any disclaimer, the term of this patent is extended or adjusted under 35 U.S.C. 154(b) by 250 days.

(21) Appl. No.: 16/086,256

(22) PCT Filed: May 20, 2016

(86) PCT No.: PCT/KR2016/005405
§ 371 (c)(1),
(2) Date: Sep. 18, 2018

(87) PCT Pub. No.: WO2017/159922
PCT Pub. Date: Sep. 21, 2017

(65) Prior Publication Data
US 2020/0289526 A1    Sep. 17, 2020

(30) Foreign Application Priority Data
Mar. 18, 2016  (KR) .................. 10-2016-0032988

(51) Int. Cl.
| | |
|---|---|
| *A61K 31/56* | (2006.01) |
| *A61K 47/64* | (2017.01) |
| *A61K 8/63* | (2006.01) |
| *A61K 6/64* | (2020.01) |
| *A61K 38/08* | (2019.01) |
| *A61K 38/10* | (2006.01) |
| *A61P 17/14* | (2006.01) |
| *A61Q 19/00* | (2006.01) |
| *A61Q 5/12* | (2006.01) |
| *A61Q 7/00* | (2006.01) |
| *C07K 7/08* | (2006.01) |
| *C07K 7/06* | (2006.01) |
| *C07K 19/00* | (2006.01) |
| *A61K 8/64* | (2006.01) |

(52) U.S. Cl.
CPC .............. *A61K 31/56* (2013.01); *A61K 8/63* (2013.01); *A61K 8/64* (2013.01); *A61K 47/64* (2017.08); *A61P 17/14* (2018.01); *A61Q 5/12* (2013.01); *A61Q 7/00* (2013.01)

(58) Field of Classification Search
CPC .......... A61K 31/56; A61K 47/64; A61K 8/63; A61K 8/64; A61K 38/10; A61K 38/08; A61P 17/14; A61Q 19/00; A61Q 5/12; A61Q 7/00; C07K 19/00; C07K 7/06; C07K 7/08
USPC ........................................ 530/500; 514/1.1
See application file for complete search history.

(56) References Cited

U.S. PATENT DOCUMENTS

| | | |
|---|---|---|
| 8,173,840 B2 | 5/2012 | Chandran |
| 8,497,241 B2 | 7/2013 | Chung et al. |
| 8,501,689 B2 | 8/2013 | Chung et al. |
| 8,729,028 B2 | 5/2014 | Chung et al. |
| 9,480,728 B2 | 11/2016 | Endo |
| 9,700,633 B2 | 7/2017 | Wang et al. |
| 9,808,511 B2 | 11/2017 | Endo |
| 9,895,302 B2 | 2/2018 | Pohlmann et al. |
| 10,023,615 B2 | 7/2018 | Bonny |
| 2004/0063628 A1 | 4/2004 | Piccariello et al. |
| 2006/0241017 A1 | 10/2006 | Chandran |
| 2011/0160131 A1 | 6/2011 | Chung et al. |
| 2011/0312884 A1 | 12/2011 | Chung et al. |
| 2012/0058137 A1 | 3/2012 | Bonny |
| 2012/0142584 A1 | 6/2012 | Bonny |
| 2012/0238498 A1 | 9/2012 | Endo |
| 2012/0245086 A1 | 9/2012 | Chung et al. |
| 2012/0289471 A1* | 11/2012 | Chandran ............ C07C 229/26 514/20.5 |
| 2014/0113887 A1* | 4/2014 | Park ..................... A61K 31/58 514/171 |
| 2014/0315810 A1 | 10/2014 | Endo |
| 2015/0118292 A1 | 4/2015 | Khesin |
| 2015/0238406 A1 | 8/2015 | Pohlmann et al. |

(Continued)

FOREIGN PATENT DOCUMENTS

| | | |
|---|---|---|
| CL | 201500502 A1 | 10/2015 |
| CN | 1698621 A | 11/2005 |

(Continued)

OTHER PUBLICATIONS

Alopecia from Merck Manual, pp. 1-9. Accessed Nov. 2, 2020. (Year: 2020).*
Alopecia Areata from Merck Manual, pp. 1-3. Accessed Nov. 2, 2020. (Year: 2020).*
Propecia from www.rxlist.com/propecia-drug.htm, pp. 1-31. Accessed Jun. 9, 2021. (Year: 2021).*
Mason et al., "Kinetics of the Reaction of Myelin Basic Protein peptide with Soluble IAu," Biochemistry, 1995, 34: 14874-14878. (Year: 1995).*
"International Search Report and Written Opinion from International Application No. PCT/KR2016/005405, dated Oct. 21, 2016.".

(Continued)

*Primary Examiner* — Julie Ha
(74) *Attorney, Agent, or Firm* — Merchant & Gould P.C.

(57) ABSTRACT

A composition for preventing hair loss and, more specifically, to a compound having a structure in which finasteride and a peptide are linked through a covalent bond and a pharmaceutical composition or a cosmetic composition for preventing hair loss or promoting hair growth comprising the same. The compound having a structure in which finasteride and a peptide are linked through a covalent bond is excellent in physiological activities such as hair loss improvement, hair growth promotion, cell growth promotion, etc., is excellent in stability in water and skin permeation, and thus can be effectively used as a composition for preventing hair loss and promoting hair growth.

4 Claims, 11 Drawing Sheets

Specification includes a Sequence Listing.

(56) References Cited

U.S. PATENT DOCUMENTS

| | | |
|---|---|---|
| 2015/0359900 A1 | 12/2015 | Wang et al. |
| 2017/0065680 A1 | 3/2017 | Endo |
| 2018/0133289 A1 | 5/2018 | Endo |
| 2019/0337988 A1 | 11/2019 | Bonny |

FOREIGN PATENT DOCUMENTS

| | | |
|---|---|---|
| CN | 102712685 A | 10/2012 |
| EP | 2275440 A | 1/2011 |
| EP | 2383283 A | 11/2011 |
| EP | 2474555 A | 7/2012 |
| JP | 10-59829 A | 3/1998 |
| JP | 2005-524677 A | 8/2005 |
| JP | 2007-510621 A | 4/2007 |
| JP | 2011-519358 A | 7/2011 |
| JP | 2012-515769 A | 7/2012 |
| JP | 2013-503856 A | 2/2013 |
| KR | 10-2008-007762 | 8/2008 |
| KR | 10-2009-0108323 A | 10/2009 |
| KR | 10-2010-0085407 A | 7/2010 |
| KR | 10-2011-0023991 A | 3/2011 |
| KR | 10-2012-0120912 A | 11/2012 |
| KR | 10-2014-0041437 A | 4/2014 |
| RU | 2570632 C2 | 1/2013 |
| WO | 03/079972 A2 | 10/2003 |

OTHER PUBLICATIONS

"Ryu et al., "Morphological Comparison of Alopecia Patients' Hair by Stress", Journal of the Korean Society of Design Culture, vol. 18, No. 2, pp. 89-100 (Jun. 2012)".

"Rizzino et al., "Regulatory Effects of Cell Density on the Binding of Transforming Growth Factor ß,Epidermal Growth Factor, Platelet-derived Growth Factor, and Fibroblast Growth Factor", Cancer Research, 48, pp. 4266-4271 (Aug. 1, 1988).".

"R. B. Merrifield, "Solid Phase Peptide Synthesis. I. The Synthesis of a Tetrapeptide", Synthesis of a Tetrapeptide, vol. 85, pp. 2149-2154 (Jul. 20, 1963).".

Second Office Action for corresponding European Patent Application No. 16894653.1 dated Oct. 2, 2020, 6 pages.

Kwak, S. et al., "Chemical modulation of bioactive compounds via oligopeptide or amino acid conjugation: Chemical Modulation of Bioactive Compounds", Biopolymers, 100(6): 584-591 (Jul. 2013).

Reissmann, S., "Cell penetration: scope and limitations by the application of cell-penetrating peptides", Journal of Peptide Science, 20(10): 760-784 (Aug. 2014).

Extended European Search Report from corresponding European Application No. 16894653.1, dated Dec. 19, 2018.

Zhao Shuang et al: "Synthesis and bioactivity of new Finasteride conjugate", Bioorganic & Medicinal Chemistry Letters, vol. 21, No. 11, Mar. 29, 2011, pp. 3439-3442.

Florence Meyer-Losie et al: "Improved Therapeutic Efficacy of Doxorubicin through Conjugation with a Novel Peptide Drug Delivery Technology (Vectocell)", Journal of Medicinal Chemistry, vol. 49, No. 23, Nov. 1, 2006, pp. 6908-6916.

Office Action for corresponding Eurasian patent application No. 201892112/28, dated Mar. 6, 2020.

Substantive Report for corresponding Chilean patent application No. 2018-002629, dated Mar. 10, 2020.

Office Action for corresponding Chinese patent application No. 201680000881.4, dated Apr. 3, 2020.

First Office Action for corresponding Japanese Patent Application No. 2018-548657, dated Dec. 10, 2019.

European Summons to Attend Oral Hearings for EP Application No. 16894653.1 dated Nov. 30, 2021.

Goswami et al., "Deferasirox-TAT(47-57) Peptide Conjugate as a Water Soluble, Bifunctional Iron Chelator with Potential Use in Neuromedicine," Biometals, 2015, 9 pages.

Miklan et al., "New Pemetrexed-Peptide Conjugates: Synthesis, Characterization and in vitro Cytostatic Effect on Non-Small Cell Lung Carcinoma (NCI-H358) and Human Leukemia (HL-60) Cells," Journal of Peptide Science, 2011, 17:805-811.

* cited by examiner

[FIG.1]
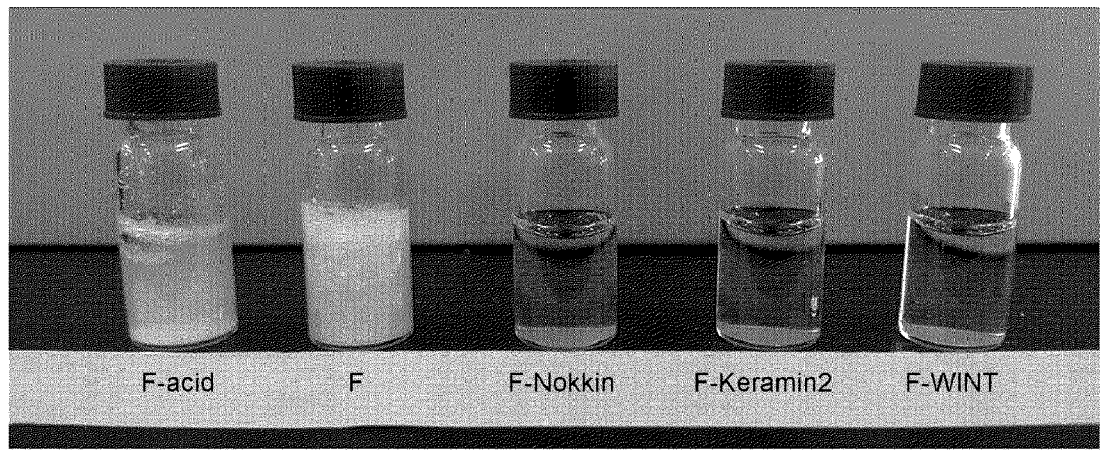
[FIG.2a]
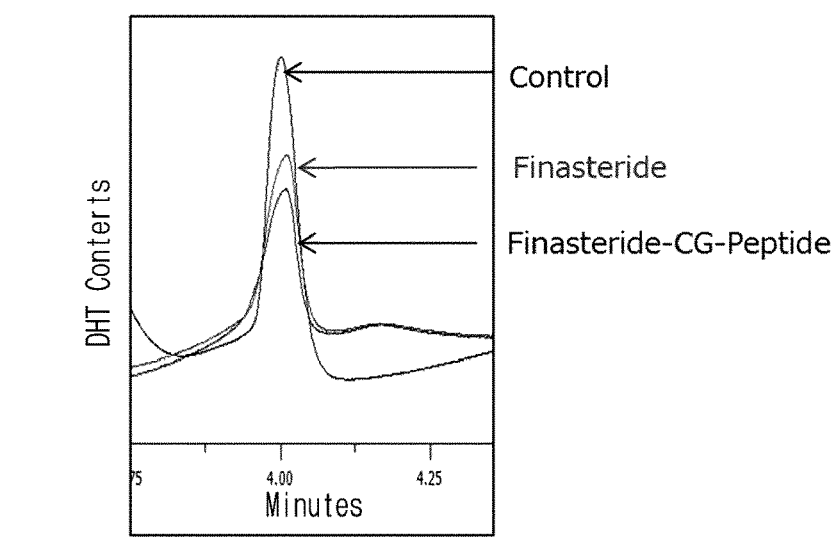
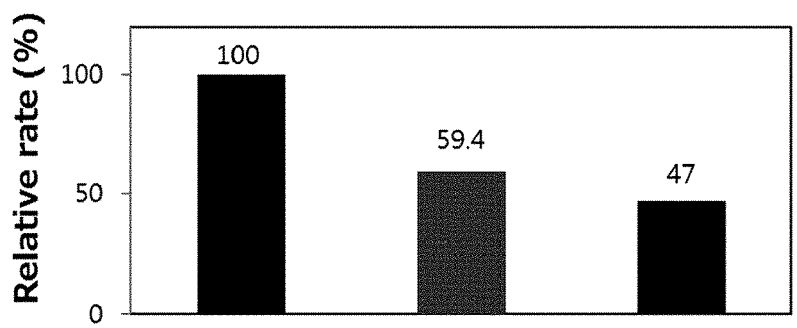
| Sample | DHT concentration (Area) | |
| --- | --- | --- |
| | Area | Related % |
| Control | 321.901 | 100 |
| Finasteride | 191.446 | 59.4 |
| Finasteride-CG-Peptide | 151.34 | 47.0 |

[FIG.2b]
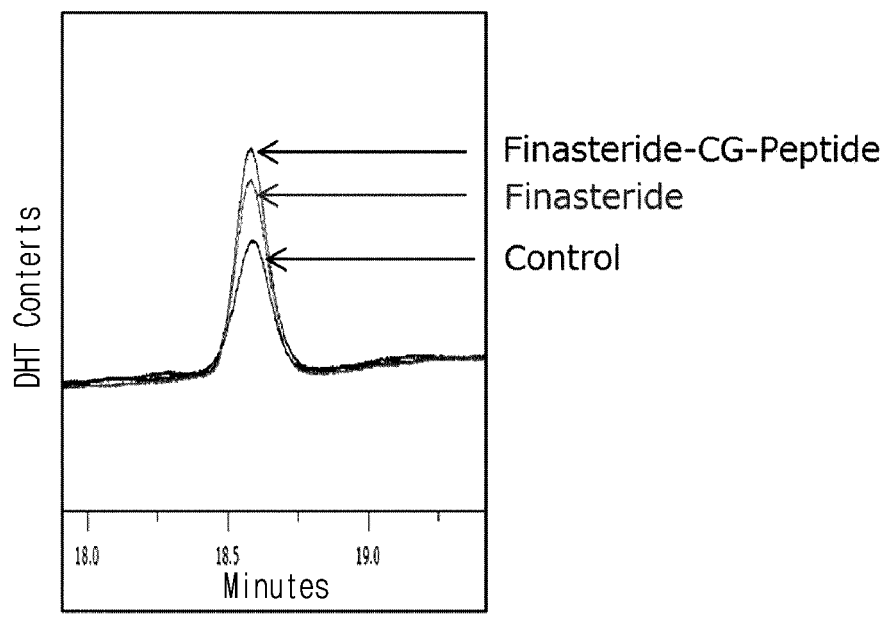
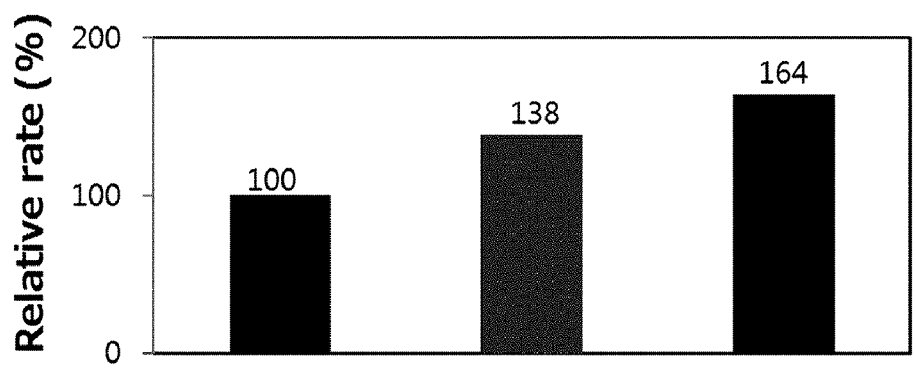
| Sample | Testosterone concentration (Area) | |
|---|---|---|
| | Area | Related % |
| Control | 97.201 | 100 |
| Finasteride | 134.179 | 138.0 |
| Finasteride-CG-Peptide | 159.426 | 164.0 |

[FIG.3a]
Control
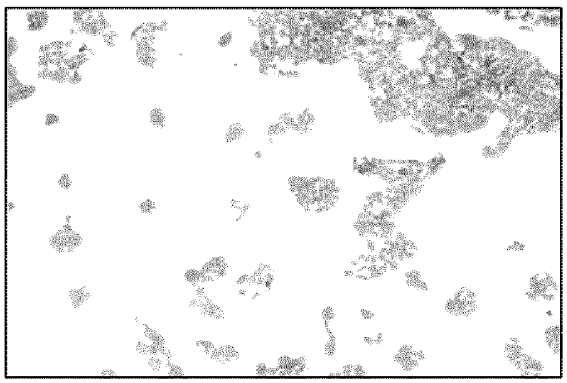
Finasteride-Keramin2 50 μM
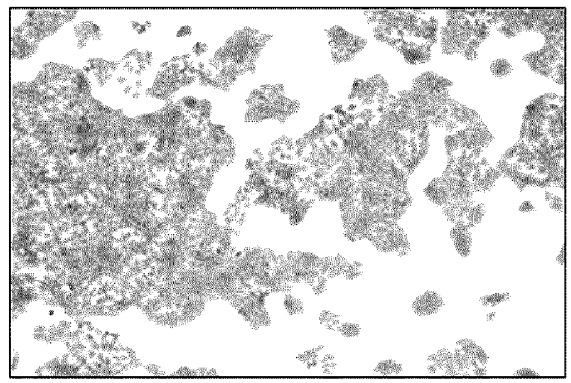
Finasteride 50 μM
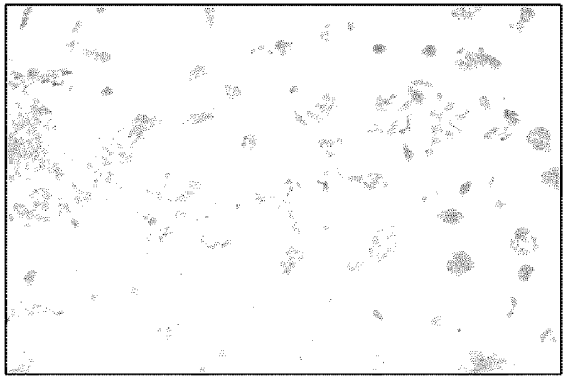
Finasteride-Nokkin 50 μM
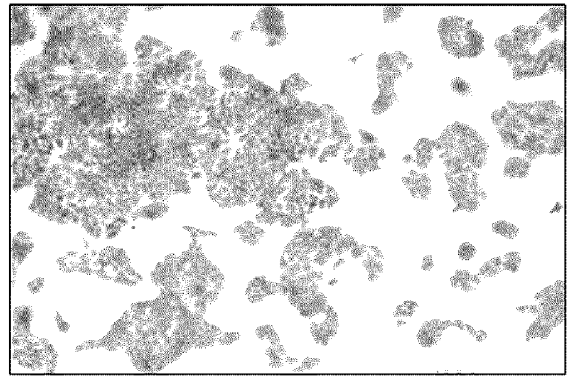
Finasteride-WINT 50 μM
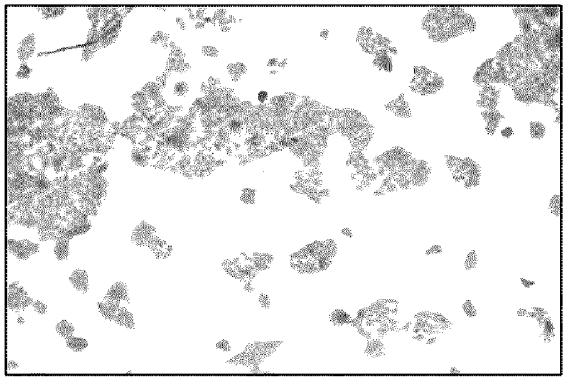
EGF 1000 μM
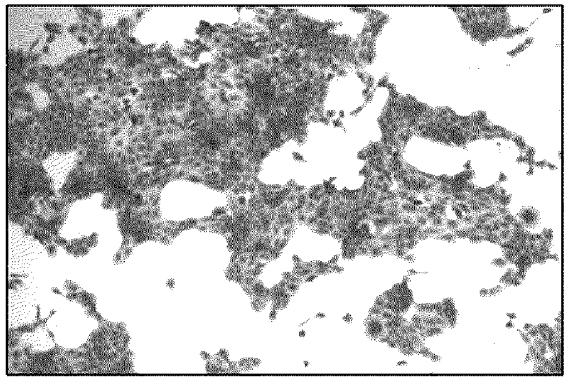

[FIG.3b]
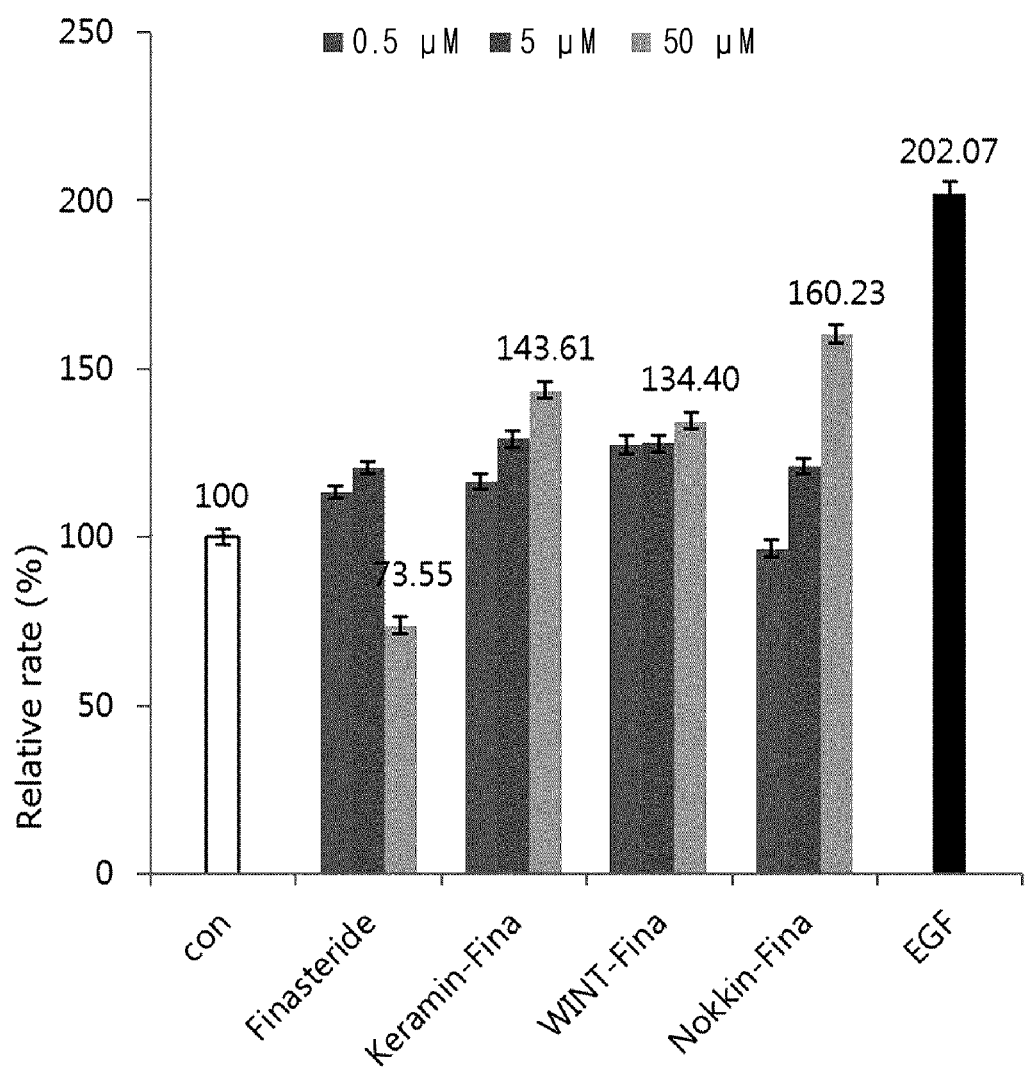

[FIG.4a]
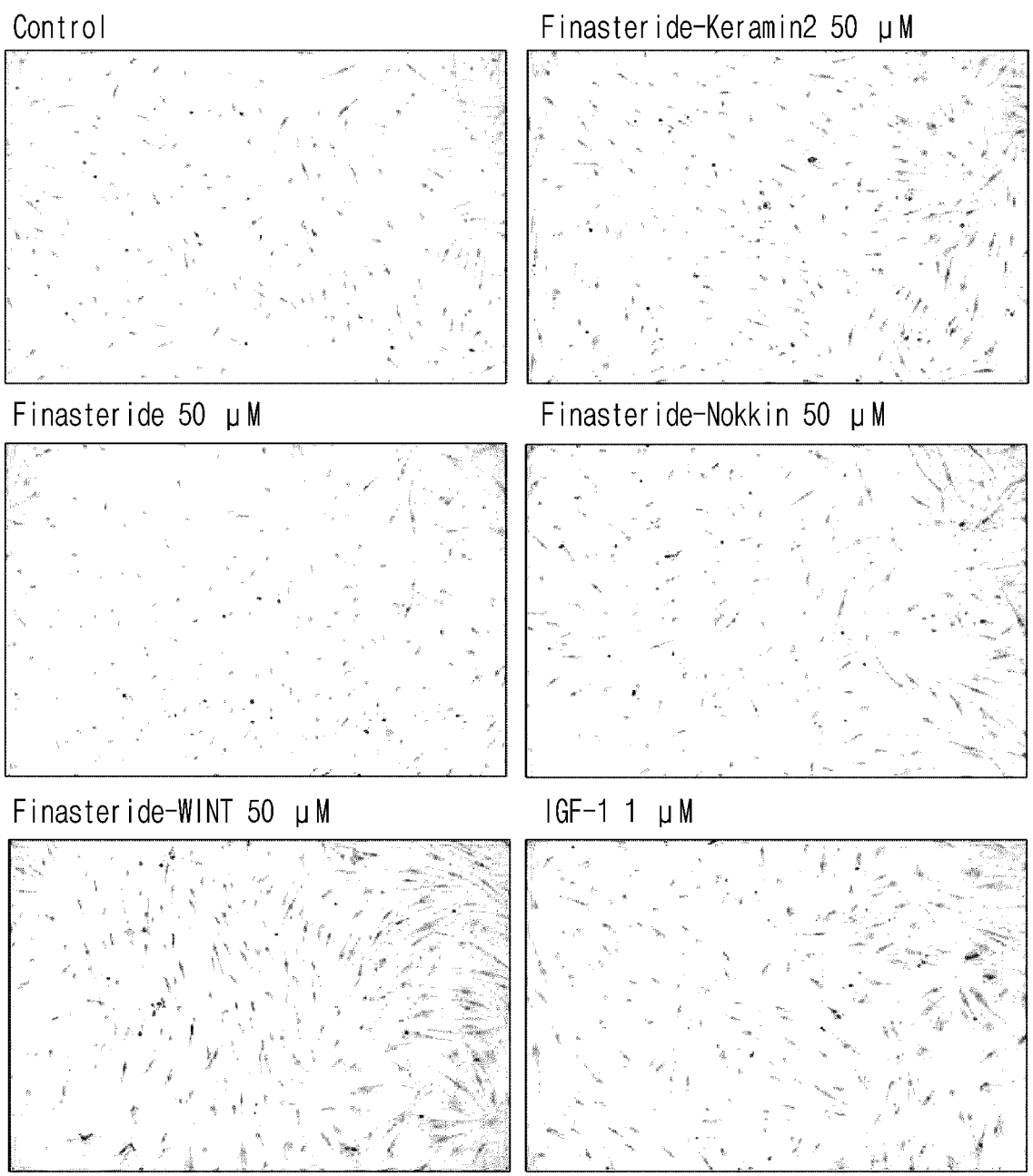

[FIG.4b]
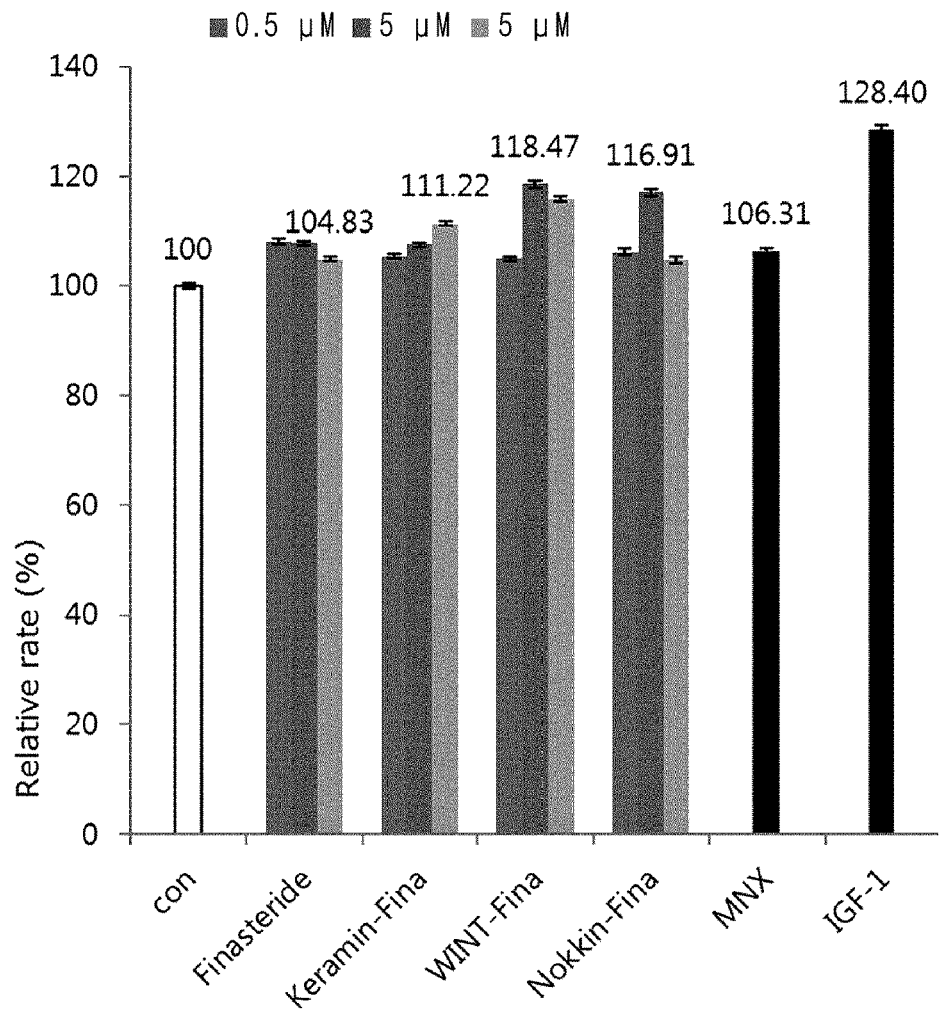
[FIG.5a]
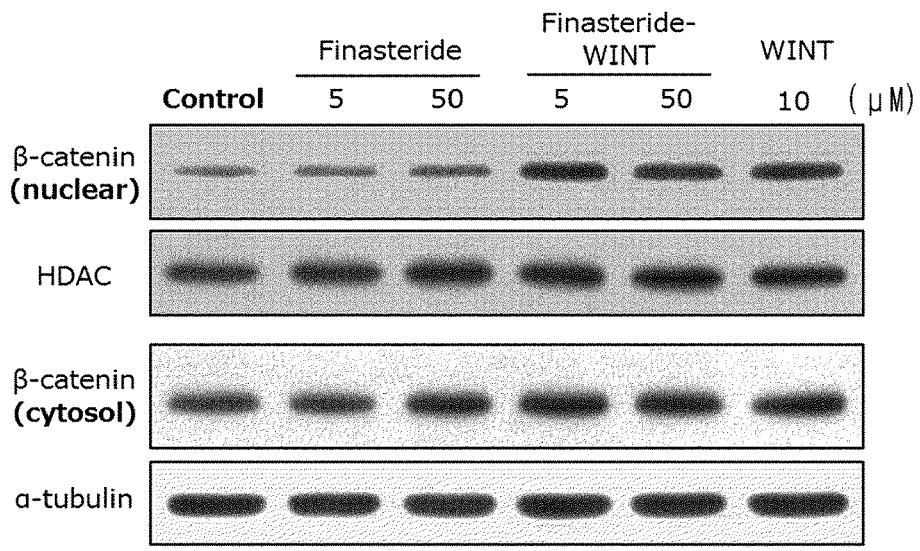

[FIG.5b]
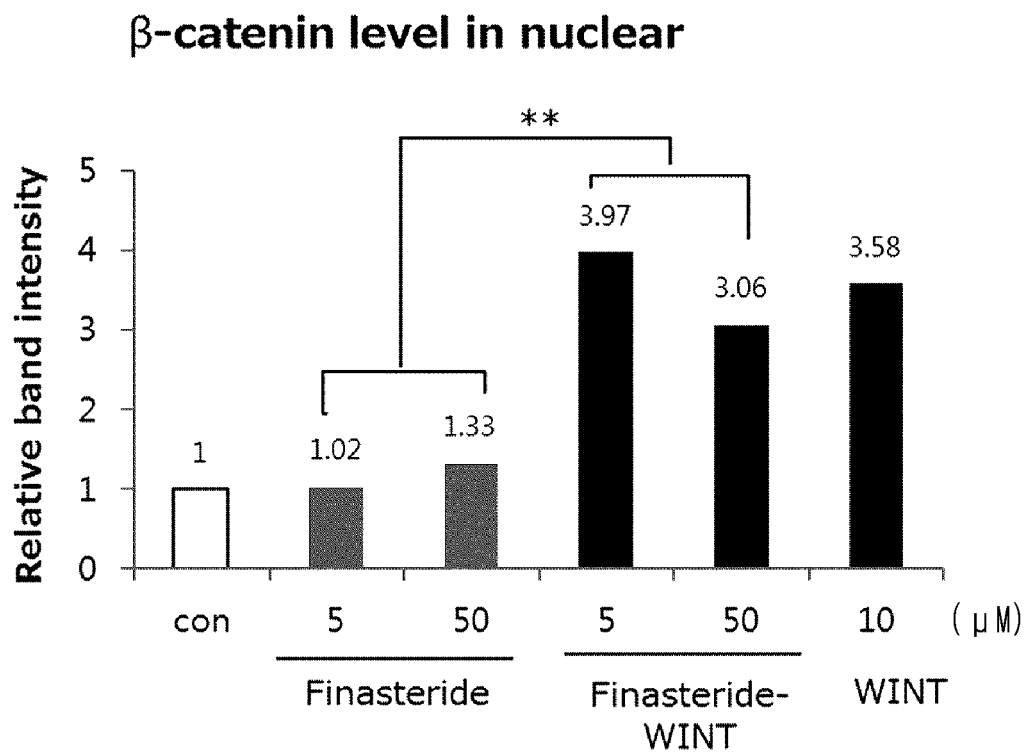
[FIG.6a]
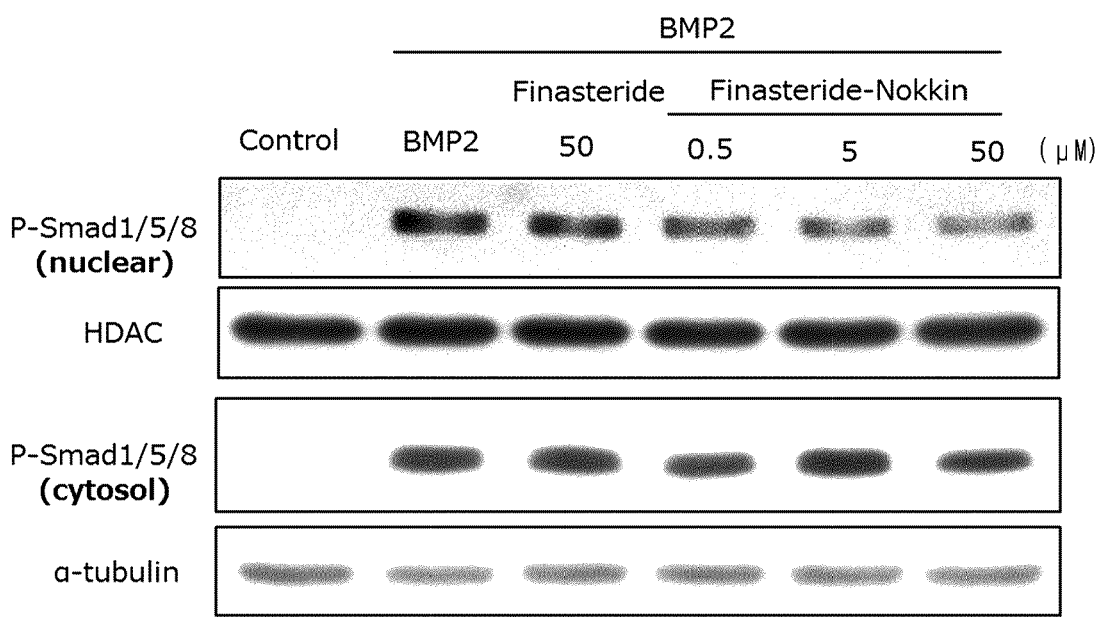

[FIG.6b]
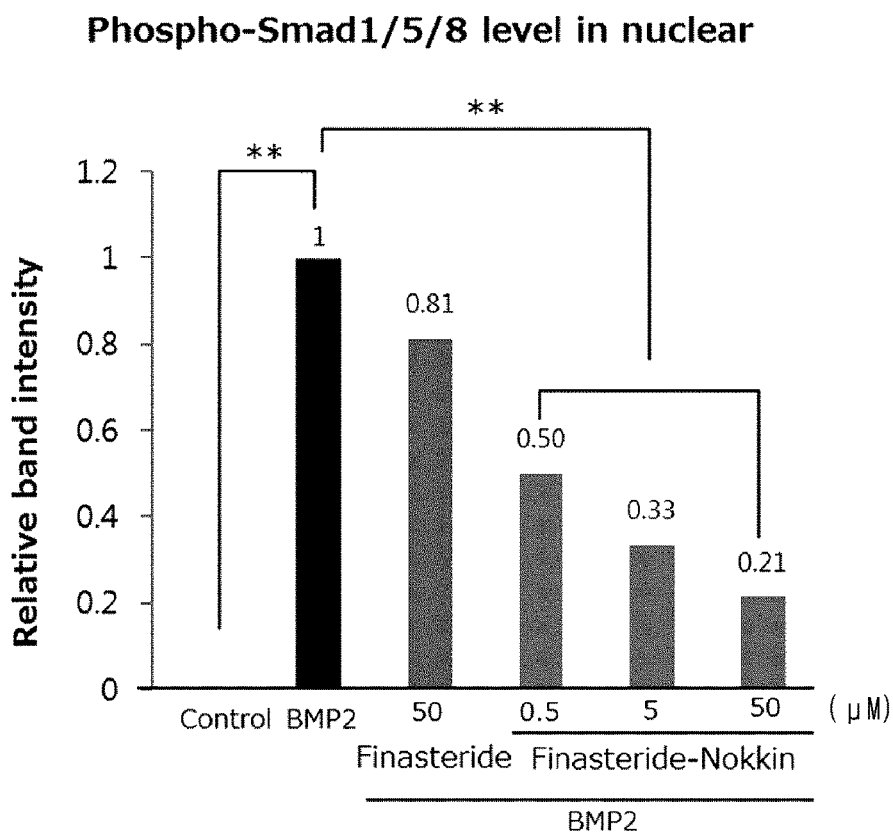
[FIG.7a]
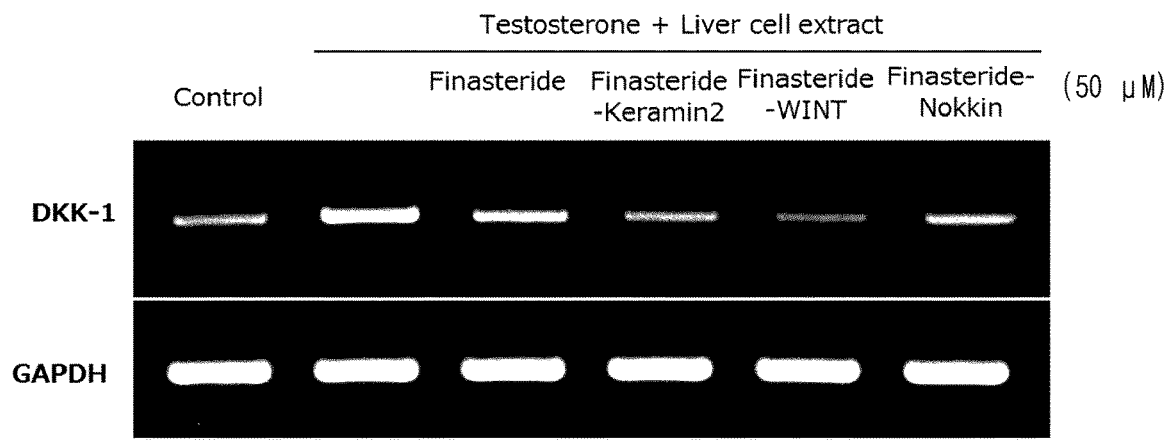

[FIG. 7b]
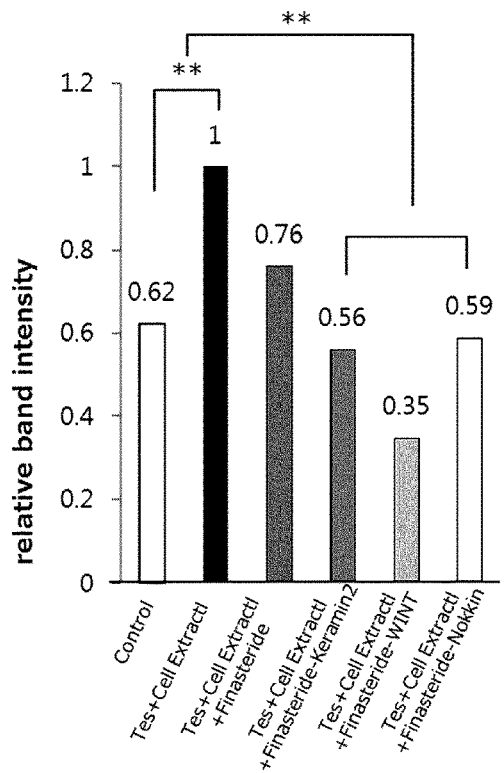
[FIG. 8a]
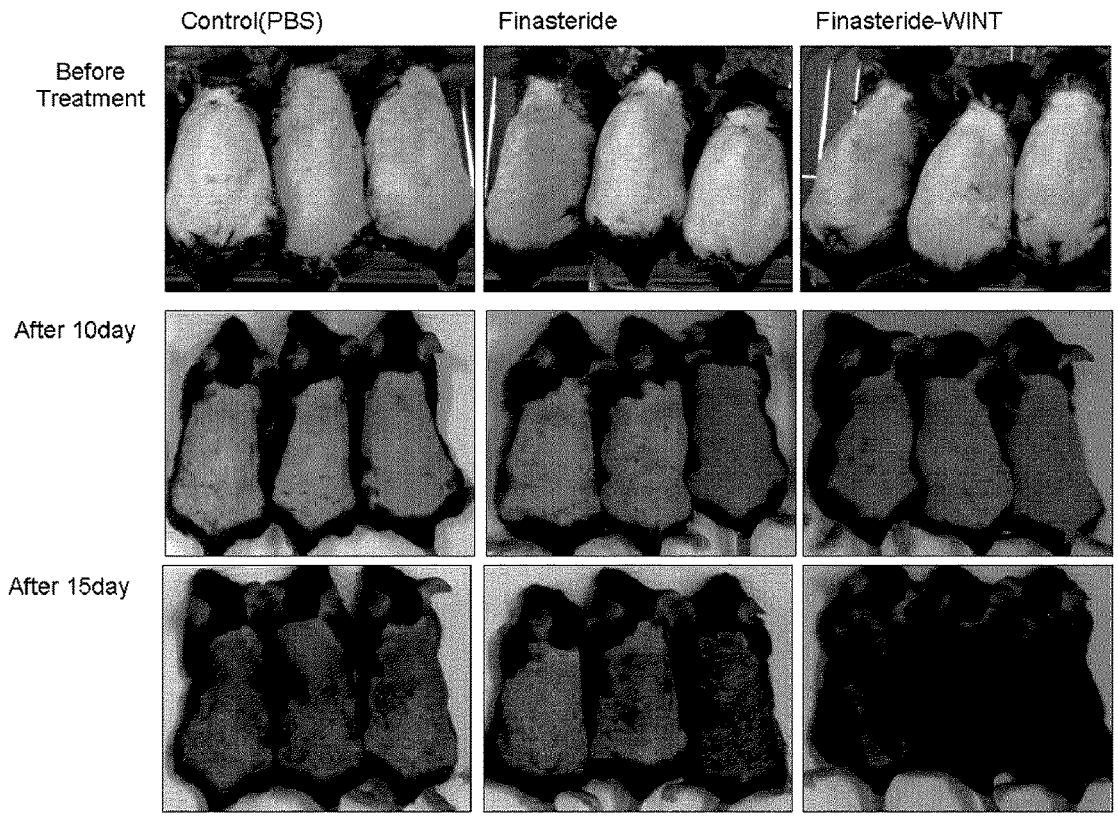

[FIG.8b]
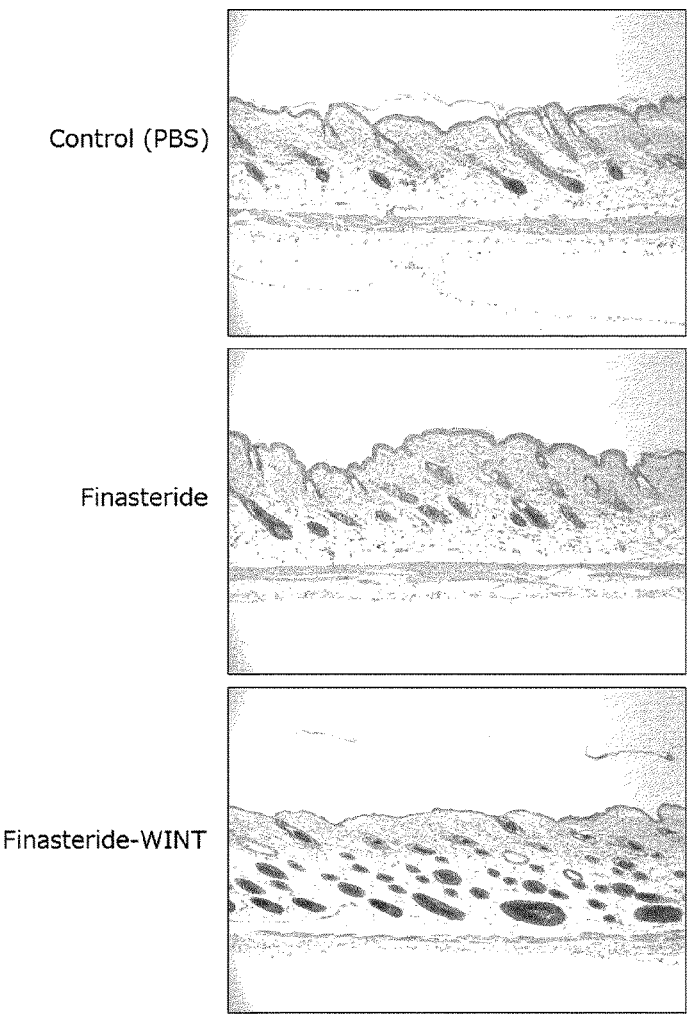
Control (PBS)
Finasteride
Finasteride-WINT
[FIG.9a]
Finasteride Treatment for 24hrs
HPLC analysis
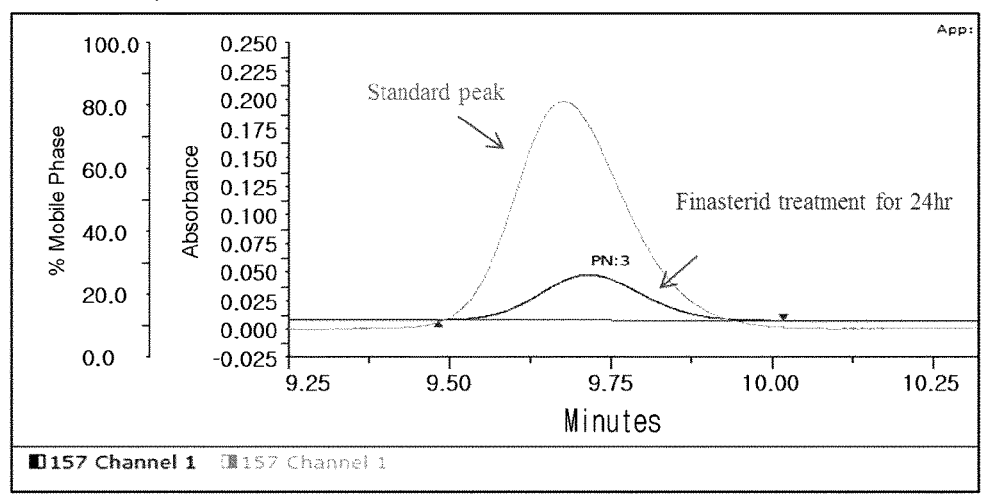

[FIG.9b]
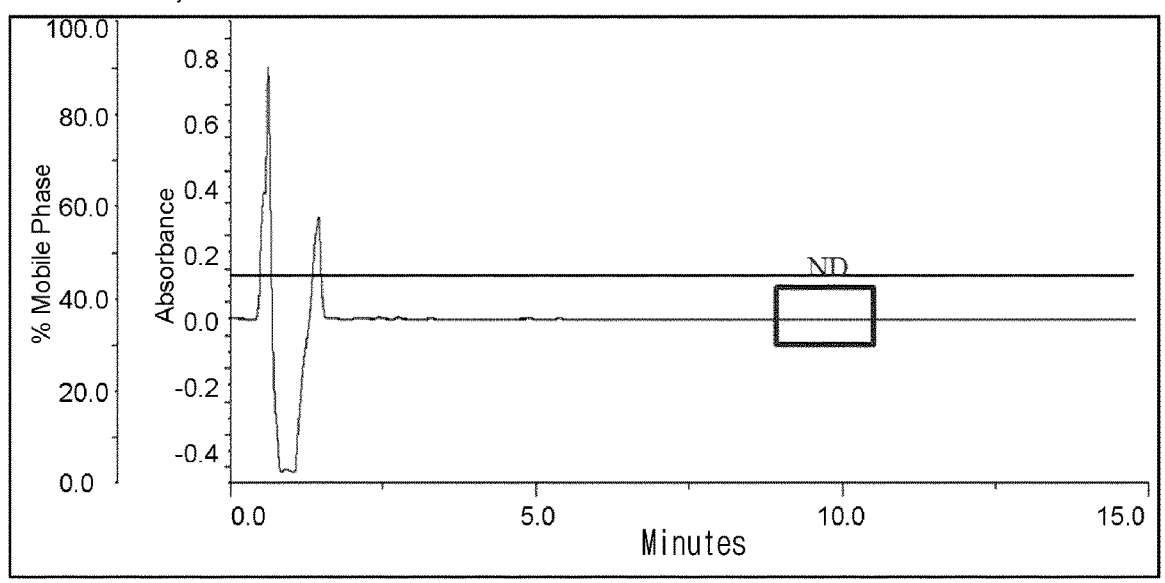
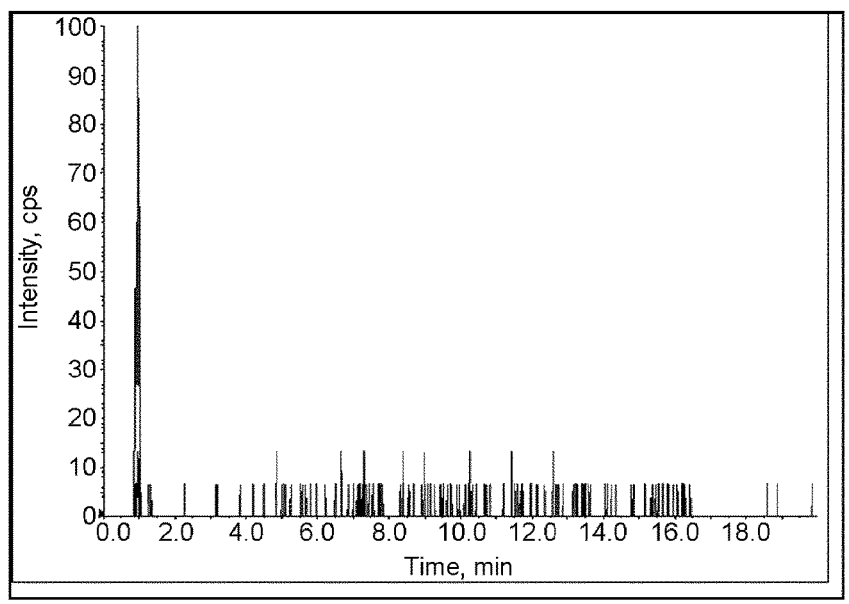

CONJUGATE OF FINASTERIDE WITH PEPTIDE

CROSS REFERENCE TO RELATED APPLICATIONS

This application is a National Stage Application of PCT/KR2016/005405, filed 20 May 2016, which claims benefit of Serial No. 10-2016-0032988, filed 18 Mar. 2016 in Korea and which applications are incorporated herein by reference. To the extent appropriate, a claim of priority is made to each of the above disclosed applications. The International Application was published in Korean on 21 Sep. 2017 as WO 2017/159922.

TECHNICAL FIELD

The present invention relates to a compound having a structure conjugating finasteride and peptide with a covalent bond, and its use for preventing hair loss or promoting hair growth.

BACKGROUND ART

Hair follicle is an organ unique to mammalian skin. The hair follicle is a down-growth of the primitive epidermis, extending into deeper layers of the skin. At the base of the hair follicle resides a plug of cells known as the follicular or dermal papilla. The papilla is essential in normal cycle of the hair follicle and in growth of the hair shaft. The hair shaft is a thread-shaped structure made of tightly coherent epithelial cells filled with keratin filaments and filament aggregating proteins.

Human hair periodically repeats the cycle of anagen, categen and telogen phases, and goes through the process of hair fall and regeneration. The hair growth cycle is regulated by hormones or many growth factors. Severe stress or malnutrition may advance the catagen and telogen phases, leading to severe hair loss.

Hair falling out from the scalp is called hair loss. Hair loss may be caused by various factors including environmental factors such as exposure to weather, light or heat, etc., and internal factors such as diseases, child birth, hormonal secretion and change, intake of drugs, nutritive conditions, etc. 5-alpha reductase is a main hormone intervening with the hair loss mechanism (Korean Patent Laid-Open No. 10-2008-0077762). 5-alpha reductase is an enzyme increasing sebum secretion by converting testosterone which is a type of androgen into dihydrotestosterone (DHT). Among the various products for preventing hair loss and promoting hair growth in the hair loss market, there are many products aiming at inhibiting the effect of the 5-alpha reductase. Hair loss may also be caused by malnutrition, dry scalp, stress, etc., in addition to enzymatic reactions (Eunju Ryu, et al., The Journal of Korean Society of Design Culture, 18(2), p. 89-100, 2012). In case of hair loss due to these reasons, hair loss may be prevented and hair growth may be promoted by supplying sufficient nutrition, performing scalp treatment and intaking or administering antioxidant substances.

Regardless of its cause, in the end, hair loss may result in exercising a great mental, social and sexual influence, together with loss of pride and self-esteem. In order to treat hair loss, until now, various substances were used as drugs, but they had disadvantages that they were too expensive or they showed a great individual difference in effect. In addition, as for cosmetic products, plant extracts which are cheaper but have a lower effect has been used, but the effect was insignificant.

Treatments and solutions for hair loss have remarkably changed over a long period of time. It became possible to hide baldness with wigs, partial wigs and hair extension, but this could not create new hair. Also, the two available drugs (minoxidil and finasteride) known up to date could delay additional hair loss, but could not be actually used for the purpose of inducing the regeneration of hair follicle. Also, as hair cosmetic products, many hair loss prevention products using plant extracts, etc. have been developed, but it has been difficult to find products that have an effect on generating new hair growth.

Various factors are linked together in the progress of hair growth and degeneration. For example, there have been many reports using a series of growth factors for promoting keratinocyte growth factors, promoting the activity of vascular endothelial growth factors, and promoting the growth of hair by inhibiting the activity of BMP type proteins. However, although such growth factors show excellent effects, an additional process of refolding and more time are required to obtain natural growth factors, and a complex purifying process for removing the pollution source originated from colon *bacillus* is required in the purification process. Also, due to its stability and high molecular weight, it could not easily surpass the protective coat of hair, and thus this together with its expensive cost deteriorated its usage.

Also, there is a method which prevents the thinning of hair and makes thinned hair thick again by the antagonism of finasteride against 5α-reductase based on the action of finasteride to androgens. As a representative example, there is Propecia (Merck U.S.A.) which was approved for its effect and stability by the U.S. Food and Drug Administration (FDA) on December 1997 as the first edible hair loss treatment and entered the market as a hair loss treatment the following year. Finasteride is a drug that inhibits 5α-reductase enzyme which converts testosterone, a type of androgen, into DHT causing hair loss. As DHT generation is inhibited by taking the drug, it plays the role of making thinned bald hair thick and long again. However, it takes months for finasteride to exert the effect of preventing hair loss. Also, as for women, there is a high possibility of congenital deformity to occur in the fetus when taking drugs, and as for men, there are fear of side effects such as loss of libido, erectile dysfunction, ejaculation disorder, etc., and pressure that the effect of preventing hair loss can be maintained only when taking the drugs for a lifetime. Thus, there are a lot of limitations for actual clinical use (Korean Patent Laid-Open No. 10-2012-0120912).

In this regard, the present inventors developed Nokkin peptide (Korean Patent Laid-Open No. 10-2010-0085407) composed of amino acid sequence of SEQ ID No. 3, Keramin2 peptide (Korean Patent Laid-Open No. 10-2009-0108323) composed of amino acid sequence of SEQ ID No. 2, and WINT peptide (Korean Patent Laid-Open No. 10-2011-0023991) composed of amino acid sequence of SEQ ID No. 1 as peptides that have more excellent stability than natural growth factors and may improve the problems caused by the large molecular weight of natural growth factors while having functions or effects the same as or similar to natural growth factors. However, the conventionally used finasteride or peptides composed of amino acid sequences SEQ ID Nos. 1 to 3 still need to be improved in the aspects of improving the effect of preventing hair loss and promoting hair growth, reducing side effects and increasing solubility in water.

DETAILED DESCRIPTION OF INVENTION

Technical Task

The present invention aims to improve the problems of the conventional hair growth solution. It is the technical task of the present invention to provide a substance for preventing hair loss and/or promoting hair growth that has the same or more excellent functions as compared with the conventional hair growth solutions such as natural growth factors or peptides composed of amino acid sequences of SEQ ID Nos. 1 to 3 or finesteride, and has excellent physiological properties such as skin permeability and stability in water.

Technical Means for Achieving Technical Tesk

In order to achieve the above technical task, the present invention provides a compound having a structure conjugating finasteride and peptide with a covalent bond.

According to an embodiment of the present invention, the peptide may be composed of 2 to 30 amino acids, preferably 5 to 20 amino acids, more preferably 8 to 15 amino acids, and more preferably 10 to 12 amino acids, but is not limited thereto.

According to an embodiment of the present invention, preferably, the peptide is a water soluble peptide, but is not limited thereto. According to a preferable embodiment of the present invention, the water soluble peptide has at least 50%, preferably at least 60%, more preferably at least 70%, more preferably at least 80%, more preferably at least 90%, and most preferably 100% of the amino acid having a hydrophilic side chain, and thus it is preferable to be high. According to an embodiment of the present invention, the amino acid having a hydrophilic side chain may be an amino acid with an electric charge, for example, arginine (Arg), histidine (His), lysine (Lys), aspartic acid (Asp) or glutamic acid (Glu), but is not limited thereto. According to an embodiment of the present invention, the water soluble peptide may comprise at least 3 amino acids with an electric charge, preferably at least 5 amino acids with an electric charge, and more preferably at least 7 amino acids with an electric charge, but is not limited thereto.

According to a preferable embodiment of the present invention, the water soluble peptide has five or less amino acids having a hydrophobic side chain, preferably four or less, more preferably three or less, more preferably two or less, more preferably one or less, and most preferably no amino acid having a hydrophilic side chain.

According to an embodiment of the present invention, the peptide may be a Nokkin peptide composed of an amino acid sequence of SEQ ID No. 1, a Keramin2 peptide composed of an amino acid sequence of SEQ ID No. 2, or a WINT peptide composed of an amino acid sequence of SEQ ID No. 3, but is not limited thereto.

Also, the present invention provides a pharmaceutical composition for preventing hair loss or promoting hair growth comprising any one of the compounds disclosed in the above.

Also, the present invention provides a cosmetic composition for preventing hair loss or promoting hair growth comprising any one of the compounds disclosed in the above.

According to an embodiment of the present invention, the cosmetic composition may have a formulation such as softening lotion, milk lotion, nourishing cream, massage cream, essence, eye cream, cleansing cream, cleansing foam, cleansing water, pack, spray, powder, hair tonic, hear cream, lair lotion, hair shampoo; hair rinse, hair conditioner, hair spray, hair aerosol, pomade, solgel, emulsion, oil, wax and aerosol, but is not limited thereto.

Advantageous Effect

The compound of the present invention having a structure conjugating finasteride and peptide with a covalent bond not only has excellent physiological activities such as preventing hair loss, promoting hair growth, promoting cell growth, etc., but also has excellent stability in water and skin permeability, and thus can be usefully used as a composition for preventing hair loss and promoting hair growth.

BRIEF DESCRIPTION OF DRAWINGS

FIG. 1 is a photograph showing the solubility of the compound of the present invention and finasteride in water.

FIGS. 2a and 2b are graphs showing the effect of the compound of the present invention and finasteride on 5α reductase activity. FIGS. 2a and 2b respectively show the relative concentration of DHT and testosterone after treatment with the compound of the present invention and finasteride.

FIG. 3a is an immunostaining photograph showing the shape and number of keratinocytes after treatment with the compound of the present invention and finasteride, and FIG. 3b is a graph showing the relative number of keratinocytes according to the concentration of the compound treated.

FIG. 4a is an immunostaining photograph showing the shape and number of human hair dermal papilla cells (HHDPC) after treatment with the compound of the present invention and finasteride, and FIG. 4b is a graph showing the relative number of keratinocytes according to the concentration of the compound treated.

FIG. 5a is a Western blot photograph showing the translocation of beta-catenin into nucleus in HHDPC cells after treatment with the compound of the present invention and finasteride, and FIG. 5b is a graph converting this into relative numerical values with respect to the negative control.

FIG. 6a is a Western blot photograph showing the expression of phospho-Smad1/5/8 in HHDPC cells after treatment with the compound of the present invention and finasteride, and FIG. 6b is a graph converting this into relative numerical values with respect to BMP2.

FIG. 7a is an electrophoretic photograph showing the expression of DKK-1 mRNA in HHDPC cells after treatment with the compound of the present invention and finasteride, and FIG. 7b is a graph converting this into relative numerical values with respect to the negative control.

FIGS. 8a and 8b are photographs confirming the effect of the compound of the present invention on hair growth through animal tests. FIG. 8a compares the growth rate of mice hair applied with finasteride and the compound of the present invention, and FIG. 8b confirms the number of hair follicle by H&E staining of the hair of the back skin of mice applied with finasteride and the compound of the present invention with H&E.

FIGS. 9a and 9b are graphs showing the skin permeability test result of the compound of the present invention.

BEST MODE FOR CARRYING OUT THE INVENTION

In order to achieve the technical task, the present invention provides a compound having a structure conjugating finasteride and peptide with a covalent bond.

The finasteride is N-(1,1-dimethylethyl)-3-oxo-(5α,17β)-4-azaandrost-1-ene-17-carboxamide, and has a formula represented by the following formula 1.

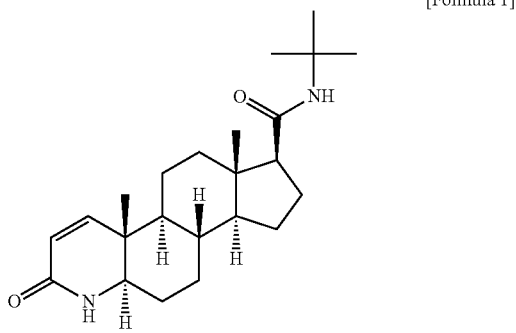

[Formula 1]

In the present invention, the term "peptide" means a linear molecule formed via peptide bond of the amino acid residues. The peptide may be prepared by biological or chemical synthesis methods generally known in the art, in particular by solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111 (1984)).

The peptide is to increase the water solubility of finasteride. In this aspect, preferably, the peptide is a water soluble peptide, but is not limited thereto. According to an embodiment of the present invention, the peptide may be composed of 2 to 30 amino acids, preferably 5 to 20 amino acids, more preferably 8 to 15 amino acids, and more preferably 10 to 12 amino acids. According to a preferable embodiment of the present invention, the peptide has at least 50%, preferably at least 60%, more preferably at least 70%, more preferably at least 80%, more preferably at least 90%, and most preferably 100% of the amino acid having a hydrophilic side chain, and thus it is preferable to be high. On the other hand, the peptide has 50% or less, preferably 40% or less, more preferably 30% or less, more preferably 20% or less, more preferably 10% or less, and most preferably 0% of the amino acid having a hydrophobic side chain, and thus it is preferable to be low. In the present invention, "amino acid having a hydrophilic side chain" refers to arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly) and proline (Pro), and "amino acid having a hydrophobic side chain" refers to alanine (Ala), valine (Val), isoleucine (Ile), leucine (Leu), methionine (Met), phenylalanine (Phe), tyrosine (Tyr) and tryptophane (Trp), but is not limited thereto. In addition to the amino acids present in the natural world, variants thereof may be used without limitation. According to an embodiment of the present invention, the amino acid having a hydrophilic side chain is preferably an amino acid with an electric charge, such as arginine (Arg), histidine (His), lysine (Lys), aspartic acid (Asp) or glutamic acid (Glu), but is not limited, thereto. According to an embodiment of the present invention, the water soluble peptide may comprise at least 3 amino acids with an electric charge, preferably at least 5 amino acids with an electric charge, and more preferably at least 7 amino acids with an electric charge, but is not limited thereto.

According to a preferable embodiment of the present invention, the peptide comprises five or less, preferably four or less, more preferably three or less, more preferably two or less, more preferably one or less, and most preferably no amino acid having a hydrophobic side chain. According to an embodiment of the present invention, the peptide may be a Nokkin peptide composed of an amino acid sequence of SEQ ID No. 1, a Keramin2 peptide composed of an amino acid sequence of SEQ ID No. 2, or a WINT peptide composed of an amino acid sequence of SEQ ID No. 3, but is not limited thereto.

According to an embodiment of the present invention, the compound of the present invention has the function of promoting growth of keratinocytes and HHDPC cells. According to an embodiment of the present invention, the compound of the present invention has the function of activating the WNT signaling pathway. According to an embodiment of the present invention, the compound of the present invention translocates beta-catenin into the nucleus.

The compound of the present invention has excellent stability by itself, but its stability may be further improved by modifying any amino acid composing the peptide conjugated to the compound. According to an embodiment of the present invention, the N-terminal of the peptide may be conjugated with a protecting group selected from the group consisting of an acetyl group, fluorenyl methoxy carbonyl group, formyl group, palmitoyl group, myristyl group, stearyl group and polyethylene glycol (PEG), to further improve the stability. According to an embodiment of the present invention, the peptide may be conjugated with a protecting group selected from the group consisting of an acetyl group, fluorenyl methoxy carbonyl group, formyl group, palmitoyl group, myristyl group, stearyl group and polyethylene glycol (PEG), to further improve the stability.

The modification of amino acid as mentioned above greatly improves the stability of the compound of the present invention. In the present invention, the term "stability" is used to encompass not only "in vivo" stability, but also "in vitro" stability such as storage stability (e.g., storage stability at room temperature). Also, the protecting group mentioned in the above protects the compound of the present invention from in vivo and in vitro attack of the proteolytic enzyme.

Also, the present invention provides a composition for treating or improving hair loss comprising the compound as an active ingredient. According to an embodiment of the present invention, the present invention provides a composition for improving skin condition comprising the peptide as an active ingredient. In the present invention, the composition may be in the form of a pharmaceutical composition or a health food, but is not limited thereto.

Since the composition of the present invention comprises the compound of the present invention as an active ingredient, common descriptions between them are omitted in order to avoid undue redundancy leading to the complexity of the specification.

According to an embodiment of the present invention, treating or improving hair loss by the compound of the present invention is promoting hair growth or growing hair. According to a preferable embodiment of the present invention, the compound of the present invention has the ability to promote the growth of keratinocytes and HHDPC cells, and promote the beta-catenin signaling pathway, which is a representative signaling pathway of WNT protein. Through animal tests carried out based on the results, it can be found that the compound of the present invention remarkably promotes hair growth. Thus, the composition of the present invention is very effective in improving hair growth and skin condition.

Also, according to an embodiment of the present invention, improving skin condition by the compound of the present invention includes, improving wrinkles, improving skin elasticity, preventing skin aging, improving skin moisturization, removing scars or regenerating skin.

Since the composition of the present invention comprises the compound of the present invention as an active ingredient, common descriptions between them are omitted in order to avoid undue redundancy leading to the complexity of the specification.

According to a preferable embodiment of the present invention, the composition of the present invention is a pharmaceutical composition comprising (a) a pharmaceutically effective amount of the compound of the present invention; and (b) a pharmaceutically acceptable carrier.

In the present specification, the term "pharmaceutically effective amount" means an amount sufficient to achieve the efficacy or activity of the compound of the present invention.

The pharmaceutically acceptable carrier of the pharmaceutical composition of the present invention which is generally used for preparation may include lactose, dextrose, sucrose, sorbitol, mannitol, starch, acacia rubber, calcium phosphate; alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but is not limited thereto. In addition to the above ingredients, the pharmaceutical composition of the present invention may further include a lubricant, wetting agent, sweetener, flavoring agent, emulsifier, suspending agent, preservative, etc. Suitable pharmaceutically acceptable carriers and preparations are described in detail in Remington's Pharmaceutical Sciences (19th ed., 1995).

The pharmaceutical composition of the present invention may be prepared in a unit dosage or multiple dosage form using a pharmaceutically acceptable carrier and/or excipient according to a method that may be easily carried out by a person having ordinary skill in the art. In this case, the formulation may be in the form of a solution in oily or aqueous medium, suspension or emulsion, or may be in the form of an extract, powder, granule, tablet, capsule or gel (e.g., hydrogel), and may further include a dispersant or a stabilizer.

The pharmaceutical composition according to the present invention may be administered orally or parenterally in clinical administration and may be used in general forms of pharmaceutical preparations. That is, the pharmaceutical composition of the present invention may be administered in various oral and parenteral dosage forms during actual clinical administration. When being formulated, a diluent or excipient such as a filler, thickening agent, binder, wetting agent, disintergrant, surfactant, etc. generally used may be used. Solid preparations for oral administration include tablets, pills, powder, granules, capsules, etc., and such solid preparations are prepared by mixing at least one excipients such as starch, calcium carbonate, sucrose or lactose, gelatin, etc. with an herbal extract or herbal fermented product. Also, in addition to simple excipients, lubricants such as magnesium stearate or talc may be used. Liquid preparations for oral administration include suspensions, solutions, emulsions, syrup, etc., and may include various excipients such as wetting agents, flavoring agents, aromatics, preservatives, etc., in addition to water and liquid paraffin, which are frequently used simple diluents. Preparations for parenteral administration include sterilized aqueous solutions, non-aqueous solutions, suspensions, emulsions, freeze-dried preparations, and suppositories. As non-aqueous solvents or suspensions, propylene glycol, polyethylene glycol, plant oils such as olive oil, injectable esters such as ethyl oleate, etc. may be used. As the base of suppositories, witepsol, Macrogol, Tween 61, cacao butter, laurin fat, glycerol, gelatin, etc. may be used.

The unit dosage form may contain, for example, 1, 2, 3 or 4 individual doses or ½, ⅓ or ¼ of an individual dose. An individual dose contains the amount of active drug which is administered in one application and this usually corresponds to a whole, ½, ⅓ or ¼ of a daily dose.

The pharmaceutical composition of the present invention may be prepared in a unit dosage or multiple dosage form using a pharmaceutically acceptable carrier and/or excipient according to a method that may be easily carried out by a person having ordinary skill in the art. In this case, the formulation may be in the form of a solution in oily or aqueous medium, suspension or emulsion, or may be in the form of an extract, powder, granule, tablet, capsule or gel (e.g., hydrogel), and may further include a dispersant or a stabilizer.

According to a preferable embodiment of the present invention, the composition of the present invention is, a cosmetic composition comprising (a) a cosmetically effective amount of the compound of the present invention; and (b) a cosmetically acceptable carrier.

In the present specification, the term "cosmetically effective amount" means an amount sufficient to achieve the efficacy of improving skin of the composition of the present invention.

The cosmetic composition of the present invention may be prepared in any formulation generally prepared in the art. For example, it may be formulated into a solution, suspension, emulsion, paste, gel, cream, lotion, powder, soap, surfactant-containing cleansing, oil, powder foundation, emulsion foundation, wax foundation and spray, etc., but is not limited thereto. More specifically, it may be prepared in various forms such as skin lotion, milk lotion, nourishing cream, massage cream, essence, eye cream, cleansing cream, cleansing foam, cleansing water, pack, spray, powder, hair tonic, hear cream, hair lotion, hair shampoo, hair rinse, hair conditioner, hair spray, hair aerosol, pomade, solution such as gel, etc., solgel, emulsion, oil, wax, aerosol, etc., but is not limited thereto.

When the formulation of the present invention is paste, cream or gel, animal oil, vegetable oil, wax, paraffin, starch, tragacanth, cellulose derivative, polyethylene glycol, silicon, bentonite, silica, talc or zinc oxide, etc. may be used as a carrier ingredient.

When the formulation of the present invention is powder or spray, lactose, talc, silica, aluminum hydroxide, calcium silicate, or polyamide powder may be used as a carrier ingredient, and especially, the spray formulation may further include a propellant such as chloro flouro hydrocarbon, propane/butane or dimethyl ether, but it is not limited thereto.

When the formulation of the present invention is a solution or emulsion, a solvent, solubilizer or emulsifier may be used as a carrier ingredient. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or sorbitan fatty acid ester may be used, but it is not limited thereto.

When the formulation of the present invention is a suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar or tragacanth, etc. may be used as a carrier ingredient, but it is not limited thereto.

When the formulation of the present invention is a surfactant-containing cleansing, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkyl amido betaine, aliphatic alcohol, fatty acid glyceride, fatty acid diethanolamide, vegetable oil, lanolin derivative, or ethoxylated glycerol fatty acid ester; etc. may be used as a carrier ingredient, but it is not limited thereto.

When the formulation of the present invention is hair shampoo, base ingredients for composing shampoo such as a thickening agent, surfactant, viscosity control agent, moisturizer, pH control agent, preservative, essential oil, etc. are mixed with the compound of the present invention. As a thickening agent, CDE may be used. As a surfactant, an anionic surfactant such as LES and an amphoteric surfactant such as coco betaine may be used. As a viscosity control agent, polyquater may be used. As a moisturizer, glycerin may be used. As a pH control agent, citric acid and sodium hydroxide may be used. As a preservative, grapefruit extract may be used. In addition thereto, essential oil such as cedarwood, peppermint, rosemary, etc., and silk amino acid, pentaol, vitamin E, etc. may be added. According to an embodiment of the present invention, with respect to 100 parts by weight of the compound of the present invention, 5 to 10 parts by weight of CDE, 30 to 40 parts by weight of LES, 10 to 20 parts by weight of coco betaine, 0.1 to 0.2 parts by weight of polyquater, 5 to 10 parts by weight of glycerin, 0.1 to 1.01 parts by weight of grapefruit extract, 0.5 to 1 parts by weight of silk amino acid, 0.5 to 1 parts by weight of pintail, 0.5 to 2 parts by weight of vitamin E, and 0.01 to 0.1 parts by weight of any one of cedarwood, peppermint, rosemary as essential oil, may be mixed, but it is not limited thereto.

The ingredients included in the cosmetic composition of the present invention include ingredients commonly used in cosmetic compositions, in addition to the compound of the present invention and the carrier ingredients as active ingredients. For example, it may further include a conventional adjuvant such as a stabilizer, solubilizer, vitamin, pigment and fragrance, but is not limited thereto.

Hereinafter, the present invention will be explained in detail with reference to the examples.

However, the following examples are provided only to illustrate the present invention, and the scope of the present invention is not limited thereby.

Example 1. Synthesis of the Compound of the Present Invention

<1-1> Synthesis of Peptide
<1-1-1> Synthesis of the Peptide of SEQ ID No. 3

700 mg, of chlorotrityl chloride resin (CTL resin; Novabiochem [0064] Cat No. 01-64-0021) was put in a reactor and stirred for 3 minutes after adding 10 ml of methylene chloride (MC). After removing the solution, 10 ml of dimethylformamide (DMF) was added. Then, after stirring for 3 minutes, the solvent was removed again. After adding 10 ml of dichloromethane (DCM) to the reactor, 200 mmole of Fmoc-Cys(trt)-OH (Bachem, Swiss) and 400 mmole of diisopropylethylamine (DIEA) were added and dissolved well by stirring. After reacting for 1 hour with stirring, the mixture was washed and dissolved with methanol and DIEA (2:1) in DCM. After reacting for 10 minutes, the mixture was washed with excess DCM/DMF (1:1). After removing the solution, followed by addition of 10 ml of DMF and stirring for 3 minutes, the solvent was removed again. After adding 10 ml of a deprotecting solution (20% piperidine/DMF) to the reactor, the mixture was stirred for 10 minutes at room temperature and then the solution was removed. After adding again the same amount of the deprotecting solution and performing reaction for 10 minutes, the solution was removed and Cys(trt)-CTL resin was prepared by washing twice with DMF, once with MC, and once with DMF, for 3 minutes, respectively.

After adding 10 ml of DMF to another reactor, 200 mmole of Fmoc-His(trt)-OH (Bachem, Swiss) and 200 mmole of Bop were added and dissolved well by stirring. After adding 400 mmole of DIEA to the reactor in two fractions, the mixture was stirred for at least 5 minutes until all the solid was dissolved. The resulting amino acid mixture solution was added to the reactor containing the deprotected resin and reacted for 1 hour at room temperature with stirring. After removing the reaction solution, followed by stirring with DMF solution 3 times, 5 minutes, respectively, the solution was removed. A small amount of the reacted resin was taken and subjected to Kaiser test (Nihydrine Test) to determine the extent of reaction. His(trt)-Cys(trt)-CTL resin was prepared in the same way as described above by deprotecting 2 times with the deprotecting solution. After sufficiently washing with DMF and MC and carrying out Kaiser test once again, amino acid attachment was carried out as follows in the same way as described above.

According to the selected amino acid sequence, chain reaction was carried out in the order of Fmoc-Cys(trt), Fmoc-Arg, Fmoc-Gln(trt), Fmoc-Val, Fmoc-Arg, Fmoc-Thr, Fmoc-Gln(trt) and Fmoc-Arg(pbf). After reacting the Fmoc-protecting group with the deprotecting solution twice for 10 minutes, respectively, the solution was removed by washing well. After performing acetylation for an hour by adding acetic anhydride, DIEA and HoBt, the prepared peptidyl resin was washed 3 times, each with DMF, MC and methanol, dried by slowly flowing nitrogen gas, completely dried in the presence of P2O5 under reduced pressure, reacted with 30 ml of a leaving solution (containing trifluoroacetic acid 95%, distilled water 2.5% and thioanisole 2.5%) for 2 hours at room temperature upon intermittent agitation. The resin was filtered and washed with a small amount of TFA solution, after which the filtrate was combined with the mother liquor. After distillation under reduced pressure to reduce the total volume to about half, precipitation was induced by adding 50 ml of cold ether and the formed precipitates were collected by centrifugation, followed by washing twice with cold ether. After removing the mother liquor, the resultant was dried sufficiently under nitrogen atmosphere to obtain 0.65 g of unpurified NH2-Arg-Gln-Thr-Arg-Val-Gln-Arg-Cys-His-Cys-OH peptide (SEQ ID No. 3) (yield: 92.6%). The molecular weight was measured as 1287.1 (theoretical value: 1286.5) using a molecular weight analyzer.

<1-1-2> Synthesis of the Peptide of SEQ ID No. 1 and SEQ ID No. 2

The peptide of SEQ ID No. 1 (Glu-Leu-Ile-Glu-His-Gly-Gly-Gly-Arg-Pro-Ala-Asp: ELIEHGGGRPAD) and the peptide of SEQ ID No. 2 (Ac-Tyr-Lys-Ser-Lys-Lys-Gly- Gly-Trp-Thr-His: Ac-YKSKKGGWTH) were synthesized using the same method as in Example <1-1-1>.

TABLE 1

| SEQ ID No. | amino acid sequence | measured value (molecular weight analyzer) | |
|---|---|---|---|
| | | measured value | theoretical value |
| 1 | ELIEHGGGRPAD | 1250.9 | 1250.35 |
| 2 | Ac-YKSKKGGWTH | 1233.8 | 1233.4 |
| 3 | RQTRVERCHC | 1287.1 | 1286.5 |

<1-2> Synthesis of the Compound of the Present Invention 1 mmol of peptidyl resin and 10 ml of 1-methyl-2-pyrrolidone (NMP) are put in a peptide reactor and reacted for 30 minutes after adding 270 mg (2.0 equiv.) of 1-hydroxybenzotriazole (HOBt) and 759 mg (2.0 equiv.) of N,N,N',N'-tetramethyl-O-(1H-benzotriazole-1-yl) uronium hexafluorophosphate; O-(benzotriazole-1-yl)-N,N,N',N'-tetramethyl uronium hexafluorophosphate. After adding 388 mg (3 equiv.) of N,N-diisopropylethylamine (DIEA) and 624 mg (2.0 equiv.) of finasteride analogue, the mixture was reacted for 24 to 72 hours at room temperature to obtain a peptidyl resin reacted by filtering. After reacting the obtained resin for 2 hours at room temperature using a cleavage solution, the resin and protecting group were removed. After recrystallizing using 10 ml (10 mmol) of diethyl ether, hybrid peptide was obtained. The reaction schemes of the compound having a structure conjugating finasteride and peptide with a covalent bond are described in detail in the following.

[Reaction scheme 1]
Reaction scheme of CG-peptide-finasteride hybrid peptide

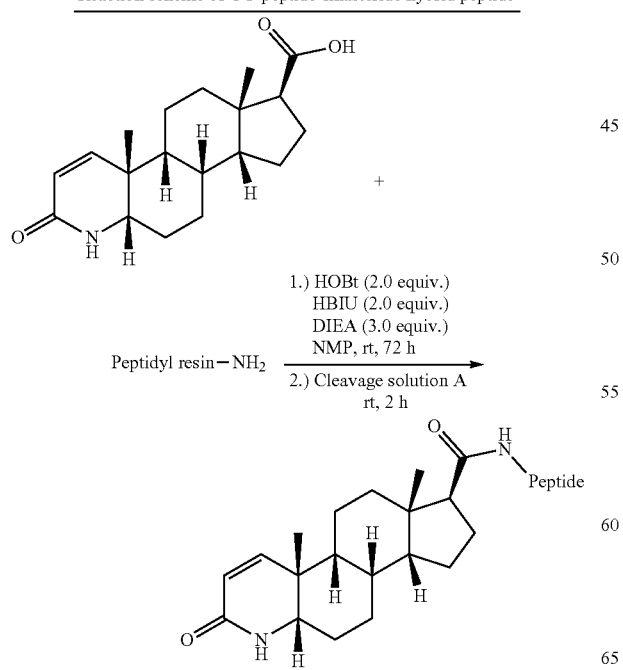

[Reaction scheme 2]
Reaction scheme of CG-Nokkin-finasteride hybrid peptide

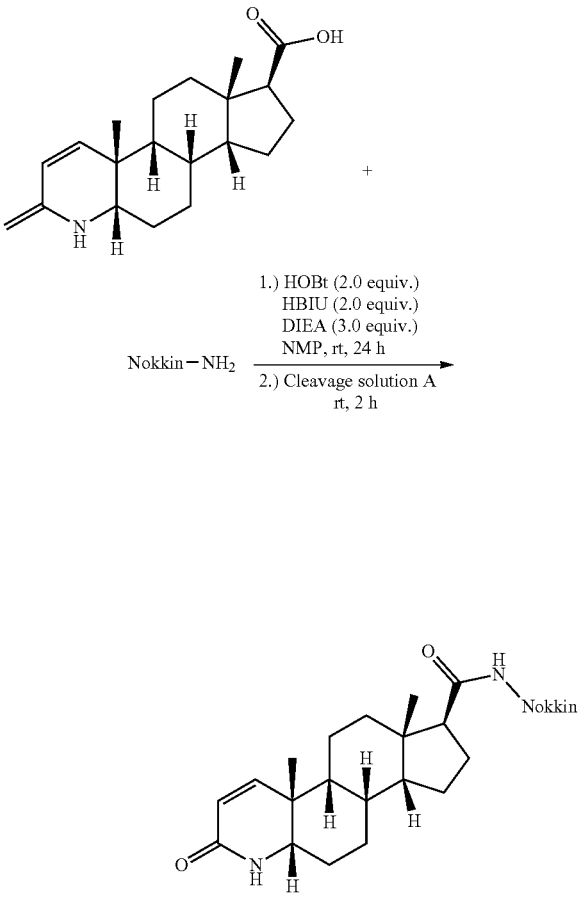

[Reaction scheme 3]
Reaction scheme of CG-Keramin2-finasteride hybrid peptide

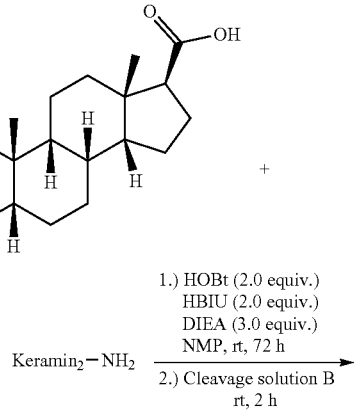

-continued

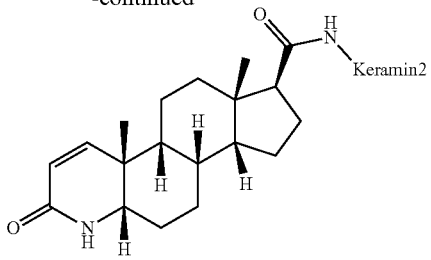

[Reaction scheme 4]
Reaction scheme of CG-WINT-finasteride hybrid peptide

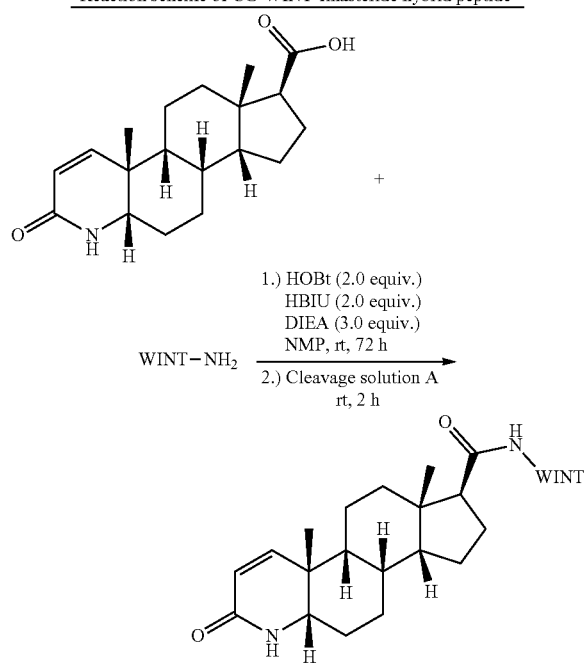

Experimental Example 1. Solubility Test of the Compound of the Present Invention Finasteride-CG-Nokkin compound (compound 1), finasteride-CG-Keramin2 compound (compound 2), finasteride-CG-WINT compound (compound 3) prepared in Example <1-2>, and finasteride are respectively dissolved in distilled water each in a concentration of 10 mg/ml.

As a result, it was confirmed that finasteride itself was hardly dissolved in water, whereas compounds 1 to 3 of the present invention were all completely dissolved in water (FIG. 1)

Experimental Example 2. Analysis on the Effect of the Compound of the Present Invention on 5α Reductase Activity In order to confirm the effect of the compound of the present invention on 5a reductase activity, first, liver cell extracts known to have a large amount of 5a reductase were collected through a protein extraction method. After reacting testosterone with finasteride or compounds 1 to 3 of the present invention, liver cell extracts were put in the corresponding solution and reacted for 1 hour at 37° C. The reactant of putting the liver cell extracts in testosterone and reacting it for 1 hour at 37° C. is the control. After the reaction is completed, the amount of testosterone and DHT were confirmed through HPLC. The HPLC analysis was carried out under the following conditions.

C18 column
UV 240 nm
flow rate: 1 ml/minute
mobile phase: A: 0.1% Formic acid in water
  B: 0.1% Formic acid in acetonitrile
gradient: 0 min B 5%~30 min B 80%

As a result, when compared with the control, the concentration of testosterone was increased when treated with finasteride and the compounds of the present invention, and the concentration of DHT was decreased in proportion thereto. Also, when compared with the case treated with finasteride, it was confirmed that the increase of testosterone concentration and decrease of DHT concentration were more remarkable when treated with the compound of the present invention (see FIGS. 2a and 2b).

Experimental Example 3. Effect of the Compound of the Present Invention on the Growth of Keratinocytes In order to analyze the similar effects and inhibitory effects of growth factors with respect to the compound synthesized in Example <1-2>, sulfohodomine B (SRB) calorimetric assay was carried out using HaCaT keratinocytes (Korean Cell Line Bank) according to the method of Rizzino et al. (Rizzino, et al. Cancer Res. 48:4266(1988)).

HaCaT keratinocytes were cultured under 5% $CO_2$ for 24 hours at 37° C. in Dulbecco's modified Eagle's medium (DMEM, Gibco, U.S.A.) containing 10% fetal bovine serum (FBS; Sigma) after inoculating each well of a 96-well plate with 3,000 cells. The cultured cell lines were treated with 1% trypsin solution to detach the cultured cell lines from the bottom of the culture flask and centrifuged to collect cell pellets. They were resuspended in FBS-free DMEM culture medium and cultured under 5% $CO_2$ for 24 hours at 37° C. After 24 hours later, the medium was changed with the same serum-free culture medium, and the cells were cultured for 72 hours under the same conditions as described above with a blank sample dissolved in 10% DMSO in sterilized condition as reference, compounds of formulae 1 to 3 of the present invention (50 μM), finasteride (50 μM), and EGF (100 nM) used as a positive reference. After removing the supernatant and fixing the cells using ethanol, the cells were washed three times with phosphate buffer saline (PBS). After removing the washing solution, and treating with calorimetric SRB solution, followed by sufficient washing with 1% acetic acid, the cells were observed under a microscope to evaluate cell viability. In addition, absorbance was measured at ultraviolet rays of 560 nm to analyze cell proliferation.

After treating the keratinocytes with the compound of the present invention and observing the morphological change in cells 72 hours later, it was confirmed that the compound of the present invention changed the growth and morphological shape of keratinocytes (FIG. 3a). Also, it was confirmed that the growth of keratinocytes was greatly increased when treated with the compound of the present invention as compared with the case treated with finasteride (FIG. 3b).

Experimental Example 4. Effect of the Compound of the Present Invention on the Growth of HHDPC Cells The effect of the compounds of the present invention on the growth of HHDPC cells (ATCC/U.S.A.) was confirmed in the same manner as in Experimental Example 3. In this case, MNX (10 uM) and IGF-1 (1 uM) were used as positive control.

As a result, it was confirmed that the compound of the present invention changed the growth and morphological shape of HHDPC cells (FIG. 4a). Also, it was confirmed that the growth of HHDPC cells was greatly increased when treated with the compound of the present invention as compared with the case treated with finasteride (FIG. 4b).

Experimental Example 5. Analysis on the Effect of the Compound of the Present Invention on Translocation of Beta-Catenin into the Nucleus 5 hours after treating HHDPC cells cultured for 48 hours with the compounds of the present invention synthesized in Example <1-2>, the effect of the compound of the present invention on the translocation of beta-catenin, which is a signal substance essential for promoting hair growth, into the nucleus by the representative signaling pathway of WNT protein was measured. The expression of beta-catenin was observed through Western blot using an antibody against beta-catenin (Santa Cruz, U.S.A.), and it was confirmed whether beta-catenin was translocated into the nucleus by immunohistochemistry using the same antibody. In particular, HHDPC cells were cultured in a $CO_2$ incubator for 24 hours at 37° C. after inoculating each well of a 6-well plate with 100,000 cells. The medium was changed into a serum-free DMEM medium, and then after treating the cells with finasteride, finasteride-WINT compound, WINT respectively in concentrations of 5 and 50 µM, the cells were cultured for, 24 hours. After extracting the nuclear and cytoplasmic protein using a protein extraction kit, Western blot was carried out under the following conditions.

preparation of 12% SDS-PAGE
loading with 15 µg of protein to SDS-PAGE
transfer to PVDF membrane
blocking with 5% dried skim milk solution for 1 hour at room temperature
reaction of 1st antibody (anti-beta-catenin antibody, anti-HDAC, anti-alpha tubulin antibody) at room temperature for 2 hours in a concentration of 1/3000
washing three times with PBST for 10 minutes
reaction of 2nd antibody at room temperature for 1 hour in a concentration of 1/5000
washing three times with PBST for 15 minutes
detection As a result, it was confirmed that when treated with the compound of the present invention, the expression of beta-catenin increased. Also, it was confirmed that beta-catenin is translocated from the cytoplasm to the nucleus by the compound of the present invention even when measuring whether beta-catenin is translocated into nucleus using immunohistochemistry in HHDPC cells, and that the compound of the present invention still exists in the cytoplasm and has activity (FIGS. 5a and 5b).

Experimental Example 6. Analysis on the Effect of the Compound of the Present Invention on Inhibition of BMP Signal Translocation 5 hours after treating HHDPC cells cultured for 48 hours with the compounds of the present invention synthesized in Example <1-2>, the effect of the compound of the present invention on the activity of phospho-Smad1/5/8, which is a signal substance essential for inhibiting hair loss, by the representative signaling pathway of BMP protein was measured. The expression of phospho-Smad1/5/8 was confirmed through Western blot using an antibody against phospho-Smad1/5/8. In particular, HHDPC cells were cultured in a $CO_2$ incubator for 24 hours at 37° C. after inoculating each well of a 6-well plate with 100,000 cells. The medium was changed into a serum-free DMEM medium, and then after treating the cells with finasteride and finasteride-Nokkin compound, respectively in concentrations of 0.5, 5 and 50 µM, the cells were cultured for 24 hours. After extracting the nuclear and cytoplasmic protein using a protein extraction kit, Western blot was carried out under the following conditions.

preparation of 12% SDS-PAGE
loading with 15 µs of protein to SDS-PAGE
transfer to PVDF membrane
blocking with 5% dried skim milk solution for 1 hour at room temperature
reaction. of 1st antibody (anti-phospho-Smad1/5/8 antibody, anti-HDAC, anti-alpha tubulin antibody) at room temperature for 2 hours in a concentration of 1/3000
washing three times with PBST for 10 minutes
reaction of 2nd antibody at room temperature for 1 hour in a concentration of 1/5000
washing three times with PBST for 15 minutes
detection As a result, it was confirmed that when treated with the compound of the present invention, the expression of phospho-Smad1/5/8 in the nucleus decreased (FIGS. 6a and 6b).

Experimental Example 7. Analysis on the Effect of the Compound of the Present Invention on the Expression of DKK-1

The effect of the compound of the present invention on mRNA expression of DKK-1, which is a representative hair loss protein expressed by DHT was confirmed. In particular, HHDPC cells were cultured in a $CO_2$ incubator for 24 hours at 37° C. after inoculating each well of a 6-well plate with 100,000 cells. After reacting testosterone with finasteride or the finasteride-Nokkin compound of compounds 1 to 3 of the present invention, finasteride-Keramin2 compound and finasteride-WINT compound, liver cell extracts were put in the corresponding solution and reacted for 1 hour at 37° C. The reactant of putting the liver cell extracts in testosterone and reacting it for 1 hour at 37° C. was used as a positive control. The medium was changed into a serum-free DMEM medium, and then after treating the cells with finasteride and finasteride-Nokkin compound, finasteride-Keramine2 compound and finasteride-WINT compound, respectively in a concentration 50 µM, the cells were cultured for 24 hours. After extracting the RNA of the cells using an RNA extraction kit, RT-PCR was carried out using the following primers.

```
1. DKK-1
forward primer:
                                      (SEQ ID No. 4)
(5')TGATGAGTACTGCGCTAGTC(3')

reverse primer:
                                      (SEQ ID No. 5)
(5')CTCCTATGCTTGGTACACAC(3')
```

-continued

2. GAPDH
forward primer:
(SEQ ID No. 6)
(5')GGAGCCAAAAGGGTCATCAT(3')

reverse primer:
(SEQ ID No. 7)
(5')GTGATGGCATGGACTGTGGT(3')

As a result, it was confirmed that the compound of the present invention further inhibited the expression of increased DKK-1 in the positive control more than the case treated with finasteride, and in particular, it could inhibit the expression of DKK-1 to a level even lower than the negative control, which was not treated with anything (FIGS. 7a and 7b).

Experimental Example 8. Hair Growth Test

The effect of the compound of the present invention on hair growth was confirmed through animal tests. In particular, the hair on the back of a 7-week old male C57BL/6 mouse was removed using hair removal cream. After preparing PBS, finasteride and the finasteride-WINT compound of the present invention in concentrations of 100 μg/ml, they were evenly applied on the back skin of mice once every day, and the color of the back skin of mice was observed by taking photographs from the point the color started to turn black.

Then, the mice were killed, and the hair on the back skin was observed through H&E staining. To this end, after collecting the back skin of mice and fixing it in 4% paraformaldehyde (PFA), paraffin embedding was carried out. After cutting the back skin of the embedded mice in a thickness of 4 μm, the number of hair follicles was confirmed through H&E staining.

As a result, it was confirmed that mice applied with the finasteride-WINT compound of the present invention clearly presented a faster rate of hair growth of the mice as compared with the mice applied with PBS or finasteride (FIG. 8a), and that the number of hair follicles increased remarkably as compared with the control and group administered with finasteride (FIG. 8b).

Experimental Example 9. Skin Permeability Test

Since finasteride is a drug controlling steroid type hormones, when it is orally administered, there may be side effects such as causing systemic toxicity by spreading through blood. Thus, if it penetrates the skin even when applied on the skin, there is a possibility for it to penetrate into the entire body and cause toxicity, and if it does not penetrate the skin, since it is left in the scalp and does not spread into the entire body, the side effects of finasteride may be inhibited. In this regard, after applying finasteride and the finasteride-WINT compound of the present invention on three dimensional artificial skin, the present inventors confirmed whether it penetrates into the skin.

To this end, finasteride and the finasteride-WINT compound of the present invention are respectively mixed in a mixed solvent of ethanol. 10%, propylene glycol 40% and purified water 50%. Franz expansion cell test was carried out using three dimensional artificial skin. Finasteride and finasteride-WINT compound solution were applied on the three dimensional artificial skin 1 ml, respectively, and left for 24 hours. After sampling the receptor chamber solution, finasteride and finasteride-WINT compound permeating the skin were detected using HPLC. The finasteride detection condition of HPLC is C18 column, UV 210 nm, flow speed 1.6 ml/min, acetonitrile:water=45:55, and the detection R.T. was 9 to 10 minutes. In order to detect the finasteride-WINT compound of the present invention, multiple reaction monitoring (MRM) assay, which is a method for detecting the corresponding molecular weight was carried out using LC-MS/MS (3200 Qtrap) equipment.

As a result, it was confirmed that the drug treated only with finasteride permeates the skin and thus was detected, and that the drug treated with the finasteride-WINT compound of the present invention was not detected with a substance permeating the skin and was left in the skin (FIGS. 9a and 9b).

Summing up the experimental results of Experimental Examples 1 to 9, it can be found that the compound of the present invention exerts the functions of promoting hair growth and inhibiting hair loss very excellently and exerts the function of anti-aging.

Formulation Example 1: Softening Lotion

The softening lotion comprising the compound of the present invention prepared in Example <1-2> and consisting of the following composition was prepared according to a general method for preparing lotion.

TABLE 2

| Ingredients | Content (weight %) |
| --- | --- |
| compound of the present invention | 2.5 |
| 1,3-butylene glycol | 6 |
| glycerin | 4 |
| PEG 1500 | 1 |
| sodium hyaluronate | 1 |
| polysorbate 20 | 0.5 |
| ethanol | 8 |
| preservative, pigment | q.s. |
| benzopenone-9 | 0.05 |
| fragrance | trace |
| purified water | balance |
| Total | 100 |

Formulation Example 2. Nourishing Cream

The nourishing cream comprising the compound of the present invention prepared in Example <1-2> and consisting of the following composition was prepared according to a general method for preparing nourishing cream.

TABLE 3

| Ingredients | Content (weight %) |
| --- | --- |
| compound of the present invention | 2.5 |
| meadow foam oil | 3 |
| cetearyl alcohol | 1.5 |
| stearic acid | 1.5 |
| glyceryl stearate | 1.5 |
| liquid paraffin | 10 |
| beewax | 2 |
| polysorbate 60 | 0.6 |
| sorbitan sesquioleate | 2.5 |
| squalane | 3 |
| 1,3-butylene glycol | 3 |
| gylcerin | 5 |
| triethanolamine | 0.5 |
| tocopheryl acetate | 0.5 |

TABLE 3-continued

| Ingredients | Content (weight %) |
| --- | --- |
| preservative, pigment | q.s. |
| fragrance | q.s. |
| purified water | balance |
| Total | 100 |

Formulation Example 3. Milk Lotion

The milk lotion comprising the compound of the present invention prepared in Example <1-2> and consisting of the following composition was prepared according to a general method for preparing lotion.

TABLE 4

| Ingredients | Content (weight %) |
| --- | --- |
| compound of the present invention | 2.5 |
| 1,3-butylene glycol | 4 |
| gylcerin | 4 |
| cetearyl alcohol | 0.8 |
| glyceryl stearate | 1 |
| triethanolamine | 0.13 |
| tocopheryl acetate | 0.3 |
| liquid paraffin | 5 |
| squalane | 3 |
| macadamia nut oil | 2 |
| polysorbate 60 | 1.5 |
| sorbitan sesquioleate | 0.5 |
| carboxyvinylpolymer | 1 |
| preservative, pigment | q.s. |
| fragrance | q.s. |
| purified water | balance |
| Total | 100 |

Formulation Example 4. Essence

The essence comprising the compound of the present invention prepared in Example <1-2> and consisting of the following composition was prepared according to a general method for preparing essence.

TABLE 5

| Ingredients | Content (weight %) |
| --- | --- |
| compound of the present invention | 2.5 |
| glycerin | 10 |
| 1,3-butylene glycol | 5 |
| PEG 1500 | 2 |
| allantoin | 0.1 |
| DL-panthenol | 0.3 |
| EDTA-2Na | 0.02 |
| hydroxyethyl cellulose | 0.1 |
| sodium hyaluronate | 8 |
| carboxyvinylpolymer | 0.2 |
| triethanolamine | 0.18 |

TABLE 5-continued

| Ingredients | Content (weight %) |
| --- | --- |
| octyldodeceth-16 | 0.4 |
| ethanol | 6 |
| fragrance, preservative, pigment | q.s. |
| purified water | balance |
| Total | 100 |

Formulation Example 5. Hair Serum

The hair serum comprising the compound of the present invention prepared in Example <1-2> and consisting of the following composition was prepared according to a general method for preparing hair serum.

TABLE 6

| Ingredients | Content (weight %) |
| --- | --- |
| compound of the present invention | 1 |
| gylcerin | 10 |
| 1,3-butylene glycol | 5 |
| PEG 1500 | 2 |
| allantoin | 0.1 |
| DL-panthenol | 0.3 |
| EDTA-2Na | 0.02 |
| hydroxyethyl cellulose | 0.1 |
| sodium hyaluronate | 8 |
| carboxyvinylpolymer | 0.2 |
| triethanolamine | 0.18 |
| octyldodeceth-16 | 0.4 |
| ethanol | 6 |
| fragrance, preservative, pigment | q.s. |
| purified water | balance |
| Total | 100 |

Formulation Example 6. Hair Toner

The hair toner comprising the compound of the present invention prepared in Example <1-2> and consisting of the following composition was prepared according to a general method for preparing hair toner.

TABLE 7

| Ingredients | Content (weight %) |
| --- | --- |
| compound of the present invention | 1 |
| gylcerin | 2 |
| 1,3-butylene glycol | 2 |
| PEG 1500 | 2 |
| allantoin | 0.1 |
| DL-panthenol | 0.3 |
| EDTA-2Na | 0.02 |
| sodium hyaluronate | 8 |
| carboxyvinylpolymer | 0.2 |
| triethanolamine | 0.18 |
| ethanol | 10 |
| fragrance, preservative, pigment | q.s. |
| purified water | balance |
| Total | 100 |

What is claimed is:

1. A compound having a finasteride moiety represented by the following structure:

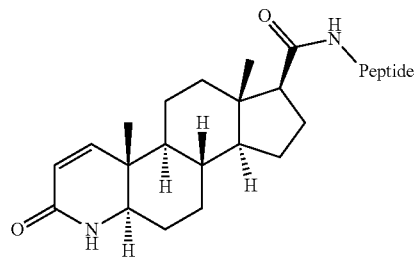

wherein the peptide is selected from the croup consisting of SEQ ID NOs: 1-3, wherein the peptide is water soluble peptide, and wherein the water soluble peptide of the compound increases the water solubility of the finasteride moiety.

2. A pharmaceutical composition for reducing hair loss or promoting hair growth comprising the compound of claim 1.

3. A cosmetic composition for reducing hair loss or promoting hair growth comprising the compound of claim 1.

4. The cosmetic composition of claim 3, which has a formulation selected from the group consisting of skin lotion, milk lotion, nourishing cream, massage cream, essence, eye cream, cleansing cream, cleansing foam, cleansing water, pack, spray, powder, hair tonic, hear cream, lair lotion, hair shampoo, hair rinse, hair conditioner, hair spray, hair aerosol, pomade, solgel, emulsion, oil, wax and aerosol.

* * * * *

SEQUENCE LISTING

<160> NUMBER OF SEQ ID NOS: 7

<210> SEQ ID NO 1

```
<211> LENGTH: 12
<212> TYPE: PRT
<213> ORGANISM: Artificial Sequence
<220> FEATURE:
<223> OTHER INFORMATION: Nokkin peptide

<400> SEQUENCE: 1

Glu Leu Ile Glu His Gly Gly Gly Arg Pro Ala Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Keramin2 peptide

<400> SEQUENCE: 2

Tyr Lys Ser Lys Lys Gly Gly Trp Thr His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: WINT peptide

<400> SEQUENCE: 3

Arg Gln Thr Arg Val Glu Arg Cys His Cys
1               5                   10

<210> SEQ ID NO 4
<211> LENGTH: 20
<212> TYPE: DNA
<213> ORGANISM: Artificial Sequence
<220> FEATURE:
<223> OTHER INFORMATION: forward primer for DKK-1

<400> SEQUENCE: 4
tgatgagtac tgcgctagtc                                               20

<210> SEQ ID NO 5
<211> LENGTH: 20
<212> TYPE: DNA
<213> ORGANISM: Artificial Sequence
<220> FEATURE:
<223> OTHER INFORMATION: reverse primer for DKK-1

<400> SEQUENCE: 5
ctcctatgct tggtacacac                                               20

<210> SEQ ID NO 6
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 6
ggagccaaaa gggtcatcat                                               20

<210> SEQ ID NO 7
<211> LENGTH: 20
<212> TYPE: DNA
<213> ORGANISM: Artificial Sequence
<220> FEATURE:
```

```
<223> OTHER INFORMATION: reverse primer for GAPDH

<400> SEQUENCE: 7
gtgatggcat ggactgtggt                                                        20
```